United States Patent [19]

Magnus et al.

[11] Patent Number: 5,442,065

[45] Date of Patent: Aug. 15, 1995

[54] SYNTHESIS OF TETRAHYDROQUINOLINE ENEDIYNE CORE ANALOGS OF DYNEMICIN

[75] Inventors: Philip D. Magnus, Austin, Tex.; Theodore Iliadis, Athens, Greece; Shane A. Eisenbeis; Robin A. Fairhurst, both of Austin, Tex.

[73] Assignee: Board of Regents, The University of Texas System, Austin, Tex.

[21] Appl. No.: 118,862

[22] Filed: Sep. 9, 1993

[51] Int. Cl.$^6$ .............. C07F 7/02; C07D 221/06; C07D 221/22
[52] U.S. Cl. ........................ 546/14; 546/79; 546/152
[58] Field of Search ............... 546/93, 79, 14

[56] References Cited

U.S. PATENT DOCUMENTS 4,924,011  5/1990  Denis et al. .......... 549/510
5,136,060  8/1992  Holton ................ 549/510

FOREIGN PATENT DOCUMENTS

WO94/18186  8/1994  WIPO ................. 305/14

OTHER PUBLICATIONS

Mangus, Philip and Fortt, Simon M., "A Rapid Entry into the Dynemicin Core Structure: Remarkable Solvent Effect on an $\eta^2$-Hexacarbonyldicobalt Propargylic Cation Cyclization", J. Chem. Soc., Chem. Commun., 7:544-545, 1991.

Nicolaou et al., "Synthesis and Biological Actions of Optically Active Enediynes Related to Dynemicin A", J. Chem. Soc., 1542-1543, 1992.

Nicolaou et al., "Designed Enediynes: A New Class of DNA-Cleaving Molecules with Potent and Selective Anticancer Activity", Science, 256: 1172-1178, 1992.

Nicolaou et al., "Synthesis and Chemistry of Dynemicin A Models", J. Am. Chem. Soc., 113:3106-3114, 1991.

Nicolaou, K. C. and Dai, W.-M., "Chemistry and Biology of the Anticancer Antibiotics", Angew. Chem. Int. Ed. Engl., 30(11):1387-1530, 1991.

Nicolaou et al., "Synthesis of Dynemicin A Models", J. Am. Chem. Soc., 112:7416-7418, 1990.

Porco et al., "Transannular Diels-Alder Route to Systems Related to Dynemicin A", J. Am. Chem. Soc., 112:7410-7411, 1990.

Semmelhack et al., "Bioreductive Alkylation as a Trigger for Toxic Effects of Dynemicin", Tetrahedron Letters, 31(11):1521-1522, 1990.

Smith et al., "Enantioselective Total Synthesis of (−)-Calicheamicinone", J. Am. Chem. Soc., 114:3134-3136, 1992.

Snyder, James P. and Tipsword, Gregory, E., "Proposal for Blending Classical and Biradical Mechanisms in Antitumor Antibiotics: Dynemicin A", J. Am. Chem. Soc., 112:4040-4042, 1990.

Wood et al., "Application of the Allylic Diazene Rearrangement: Synthesis of the Enediyne-Bridged Tricyclic Core of Dynemicin A", 114:5898-5900, 1992.

(List continued on next page.)

Primary Examiner—Alan L. Rotman
Attorney, Agent, or Firm—Arnold, White & Durkee

[57] ABSTRACT

A process is described for the preparation of the core azobicyclo[7.3.1]tridecaenediyne moiety of the antitumor antibiotic dynemicin. The synthesis allows efficient production of the enediyne as a stable, compound in good yield from the adamantyl N-protected azabicyclo[7.3.1]tridecadiyne. The adamantyl protecting group is employed in the starting material, N-adamantyl dihydroquinoline or N-adamantyl 6-methoxy quinoline. Also disclosed are process for the synthesis of 3-hydroxy-6-methoxyquinoline and several N-substituted derivatives of azobicyclo[7.3.1]tridecaenediyne. Solid tumor and leukemia assays were performed on the analogs of dynemicin. The results suggest a method that these compounds will useful in treating certain types of leukemias and solid tumors. The disclosed synthesis provides a route to new dynemicin intermediates and analogs which will allow development of second and third generation dynemicins.

1 Claim, 10 Drawing Sheets

U.S. PATENT DOCUMENTS

Haseltine et al., "Total Synthesis of Calicheamicinone: New Arrangements for Actuation of the Reductive Cycloaromatization of Aglycon Congeners", *J. Am. Chem. Soc.*, 113:3850–3866, 1991.

Kamei, et al., "Dynemicins, New Antiobiotics with the 1,5-Diyn-3-ene and Anthraquinone Subunit", *J. of Antibiotics*, 44(12):1306–1311, 1991.

Konishi et al., "Dynemicins , New Antibiotics, with the 1,5-Diyn-3-ene and Anthraquinone Subunit", *J. of Antibiotics*, 44(12):1300–1305, 1991.

Konishi et al., "Crystal and Molecular Structure of a Dynemicin A: A Novel, 1,5-Diyn-3-ene Antitumor Antibiotic", *J. Am. Chem. Soc.*, 112:3715–3716, 1990.

Konishi et al., "Dynemicin A, A Novel Antibiotic with the Anthraquinone and 1,5-Diyn-3-ene Subunit", *The Journal of Antibiotics*, LXII(9):1449–1452.

Langley, et al., "The Dynemicin–DNA Intercalation Complex. A Model Based on DNA Affinity Cleavage and Molecular Dynamics Simulation", *J. Am. Chem. Soc.*, 113:4395–4403, 1991.

Magnus, et al., "Synthetic and Mechanistic Studies on the Antitumor Antibiotics Esperamicin $A_1$ and Calicheamicin $\gamma_1$: Synthesis of 2–Ketobicyclo[7.3.1] Enediyne and 13–Ketocyclo[7.3.1] Enediyne Cores Mediated by $\eta^2$ Dicobalt Hexacarbonyl Alkyne Complexes. Cycloaromatization Rate Studies", *J. Am. Chem. Soc.*, 114:2544–2559, 1992.

Magnus et al., "Synthetic and Mechanistic Studies on the Antitumor Antibiotics Esperamicin $A_1$ and Calicheamicin $\gamma_1$. Oxidative Functionalization of the 13–Ketobicyclo[7.3.1] tridecenediyne Core Structure: Construction of the Allylic Trisulfide Trigger", *J. Am. Chem. Soc.*, 114:2560–2567, 1992.

1(R=H)
2(R=Ac)

3234

2585

4230

5582

4229

SYNTHESIS OF TETRAHYDROQUINOLINE ENEDIYNE CORE ANALOGS OF DYNEMICIN

The United States Government owns rights in the present invention pursuant to grant No. CHE 9025126 from the National Science Foundation.

BACKGROUND OF THE INVENTION

1. Field of the Invention

The invention is concerned with novel antitumor/antibiotic compounds related to dynemicin which contain a core tetrahydroquinoline enediyne structure and to novel methods of synthesis of analogs and derivatives of these compounds. Also disclosed are pharmaceutical compositions employing various of the new compounds as antitumor agents.

2. Description of Related Art

Enediyne anticancer antibiotics are a recently discovered class of compounds with potent biological activities. This class of compounds includes neocarzinostatin, esperamicin, and, more recently, dynemicin, as well as calicheamicin. The enediyne moiety is a bicyclo [7.3.0]dodecaenediyne chromophoric system. The unusual molecular architecture contributes to the exceptional biological activity and mode of action of enediyne compounds which are believed to exert their effect as DNA cleaving compounds operating through a free radical mechanism. Such cleaving properties are derived from the ability to generate $Sp^2$ carbon centered radicals after activation (Nicolaou and Dai, 1991).

The different groups of enediyne anticancer antibiotics exhibit similar biological activities, but may differ significantly in target and toxicity. Neocarzinostatin was originally isolated from a culture of *Streptomyces carzinostaticus*. Compounds of this class exhibit potent antitumor antibacterial action. The calicheamicins are isolated from *Micromonospora echinospora* ssp. calichensis. This subclass of compounds is highly active against both gram positive and gram negative bacteria and also exhibits unusual high activity against murine tumors such as P338, L1210 leukemias and solid neoplasms such as COLN26 and B-16 melanoma. Esperamicins have been isolated from cultures of *Actinomadura verrucosospora* and are similar in their activities to the calicheamicins. Structurally, the esperamicins contain a bicyclo [7.3.1]tridecaenediyne ring system, an allylic trisulfide (or tetrasulfide), a 1,5-diyn-3-ene moiety as pan of the ring system, and an $\alpha,\beta$-unsaturated ketone in which the double bond is at the bridgehead of the bicyclic core. These compounds are extremely potent anticancer agents and exhibit activity against several murine tumor models, including P388, B16, and 5076.

A more recently discovered class of enediynes are the dynemicins. These violet-colored antibiotics were isolated from fermentation cultures of *Micromonospora chersina*. Studies in vitro and in vivo have demonstrated that these compounds are active against a variety of cancer cell lines. They have been shown to significantly prolong the life of mice inoculated with P388 leukemia and B16 melanoma cells. The dynemicin family of compounds combines low toxicity with good in vivo antibacterial activity. Deoxydynemicin, like the parent dynemicin, is also biologically active. Structurally, the dynemicins include a ten-membered ring with a 1,5-diyn-3-ene bridge; however, they differ structurally from other related families in having an anthraquinone chromophore.

1,5-diyn-3-ene antibiotics have generated considerable interest and challenge to synthesize new active compounds which have the unique 1,5-diyn-3-ene core. Several reports have indicated successful synthesis of the core diyne structure. Calicheamicinone has been totally synthesized (Hazeltine et al., 1991). The synthesis employed application of the Becker Alder reaction to obtain an appropriately substituted brominated benzaldehyde, an in situ protection, and an intramolecular Emmons-like closure in an annulation procedure. The final product, calicheamicinone, represents the aglycone moiety of calicheamicin $\gamma$-1 and esperamicin $a_1$.

The aglycon portion of calicheamicin $\gamma$-1 has also been synthesized (Smith et al., 1992). In that synthetic approach, the molecule was synthesized via an intramolecular alkenyl nitrile oxide dipolar cycloaddition reaction leading directly to incorporation of the full functionality of the aglycon.

Other approaches to the synthesis of the ene-diynes of esperamicin/calicheamicin have provided a synthesis of 2-ketobicyclo [7.3.1]enediyne and 13-ketocyclo [7.3.1]enediyne through the use of $\eta^2$ dicobalt hexacarbonyl, alkyne complexes. This synthesis is based on complexing the 10,11-acetylenic bond with a dicobalt hexacarbonyl compound (Magnus and Fortt, 1991).

Several approaches to a simple and efficient route to a dynemicin A model system have been reported. In contrast to the above strategies, a transannular Diels-Alder route has resulted in polycyclizations to dynemicin-type molecules (Porco et al., 1990). Other synthetic routes have been reported (Nicolaou et al., 1990). Two novel dynemicin A compounds containing the epoxide and the ene-diyne functionalities of the parent compound were synthesized with either hydrogen or hydroxyl at one of the bridgehead positions. Other model dynemicin A compounds have been prepared starting from 7,8,9,10-tetrahydrophenanthridine. The compounds produced in these syntheses were N-protected derivatives (Nicolaou et al., 1991). The N-protected model systems failed to exhibit any activity when incubated with $\phi$x 174 DNA. However, some activity was observed when the N protecting group was removed. The free amine was unstable although activity in crude mixtures caused double-stranded DNA cleavage similar to that observed for the parent compound dynemicin A.

An alternate synthesis of the core tetrahydroquinoline enediyne structure using $\beta^2$ hexacarbonyl dicobalt acetylene complexes has been reported (Magnus & Fortt, 1991). An important step in this synthesis was complexation of one of the intermediates as a hexacarbonyl dicobalt complex. By employing a cation solvating solvent for the formation of the azabicyclo [7.3.0]diynene, a stable azabicyclo [7.3.1]tridecaenediyne core structure was obtained. In another approach, a transannular Dieis-Alder polycyclization and an allylic diazine rearrangement have provided an intermediate that was transformed to the ene-diyne bridged tricyclic core of diynemicin A (Wood et al., 1992).

While a number of approaches to the synthesis of enediynes and particularly aimed at the total synthesis of diynemicin A have been explored, there exists a need for analogs containing the core enediyne bridged tricyclic diynemicin A core. An improved synthesis would provide more efficient entry to novel compounds with expanded antibiotic and antitumor activities.

SUMMARY OF THE INVENTION

The present invention seeks to overcome these problems and other drawbacks inherent in the prior art by providing an improved synthesis of the azabicyclo[7.3.1]tridecaenediyne core structure of the antitumor antibiotic dynemicin. The invention also relates to analogs and derivatives of the enediyne which show in vivo antitumor activity. Also disclosed is an efficient synthesis of 3-hydroxy-6-methylquinoline which may be used as a starting compound for the synthesis of dynemicin core analogs and derivatives.

In general, the method relates to a process for preparing azobicyclo[7.3.1]tridecaenediyne or more specifically in chemical terms N-[(methoxy)carbonyl]-15-keto-13-methoxy-10-aza-14a, 10a-benzobicyclo[7.3.1]tridec-3,7-diyn-5-ene. The process involves the steps of first reacting an O-protected 3-hydroxyquinoline with a magnesioacetylide prepared from the tetrahydropyranyl ether of Z-hept-4-ene-2,6-diyn-1-ol. Protection of the 3-hydroxyl group is preferably with a silyl group such as trimethylsilyloxyl, tri-isopropylsilyloxyl or, preferably, 3-t-butyldimethylsilyloxyl. A chloroformate is added to the reaction mixture to form an N-protected dihydroquinoline.

N-substitution is readily effected by treating one of the hydroxy quinoline starting materials with a chloroformate to obtain an alkyl such as methyl, ethyl, etc., benzyl, phenyl, cholesterol, menthyl or, preferably, adamantyl carbamate. The inventors have discovered that the N-adamantyl protecting group is quite unexpectedly preferred over other protecting groups because it may be readily hydrolyzed to form the benzobicyclo[7.3.1]tridec-3,7-diyn-5-ene dynemicin core. Other protecting groups such as N-methoxycarbonyl or chloroethyl groups are not satisfactory because basic or nucleophilic conditions are required for their removal. These reaction conditions result in low yields because of extensive destruction of the enediyne core. Under basic conditions, an aromatized adduct is formed. In contrast, the adamantyl carbamate group is readily removed with trifluoroacetic acid and dichloromethane at room temperature to give high yields of the deprotected amine, typically in yields exceeding 80%.

The silyloxy protecting group of the N-adamantyl protected 6-alkoxy silyl ether-protected magnesioacetylide is readily removed to afford the primary alcohol by using such reagents as pyridinium tosylate/ethanol (the Grieco procedure).

The acetylide is then treated with $Co_2(CO)_8$ to form a hexacobalt $\eta^2$-$Co_2(CO)_6$ complex. The major product is a cobalt complex formed at the 3-4 acetylenic position but some complex at the acetylenic 7-8 position is also formed. The undesired regioisomer at the 7-8 position may be recycled by oxidation to the diacetylenic compound which is then treated with dicobaltoctacarbonyl. While ceric ammonium nitrate is the preferred oxidizing agent, other similar oxidants may be used including, for example, any transition metal oxidant, N-oxides of amines, $Fe(NO_3)_3$ or $FeCl_3$.

The advantage of the cobalt complex is that it is readily cyclized in cation-solvating solvents. Other solvents such as $CH_2Cl_2$ (trifluoromethanesulfonic anhydride-2,6-di-tert-butyl-4-methylpyridine) at low temperatures fail to promote cyclization. This unusual solvent effect on $\eta^2$-hexacarbonyldicobalt propargylic cation cyclization has been described (Magnus and Fortt, 1991).

The last step in the process to achieve the benzobicyclo[7.3.1]tridec-3,7-diyn-5-ene molecule is to remove the adamantyl N-protecting group. As previously discussed, the adamantyl group is readily removed. The free amine is stable and obtained in an overall yield of at least 80%. Surprisingly, removal of the N-protecting group provides a stable, free amine. Other protecting groups such as ethyl chloroformate, cannot be removed without substantially destroying the bicyclo ring system. In retrospect, the inventors believe that while the chloroformate group is generally removable under acidic conditions, it is such conditions that promote instability in the tridecaenediyne molecule thereby leading to destruction of the bicyclo ring. On the other hand, groups such as adamantyl which are readily removed under electrophilic conditions leave the core structure intact. It has been found that the adamantyl group is superior to other groups tested; however, it is possible that other alicyclic bicyclo or fatty acid analogs might also provide good results.

In a similar manner, 15-keto- 10-aza- 14a, 10a-benzobicyclo[7.3.1]tridec-3,7-diyn-5-ene may be readily synthesized by reacting a 3-hydroxy protected quinoline with hydroxyl protected magnesioacetylide and adamantyl chlorocarbonate and following the steps previously discussed.

In an alternate synthesis of the 13-methoxy benzobicyclo[7.3.1]tridec-3,7-diyn-5-enes, it is not necessary to use a 6-methoxy 3-hydroxyquinoline as a starting material. The 13methoxy compounds may be prepared by forming an epoxide across the 3,4-position before complexation to form the cobalt complex. The epoxide may be formed by peroxidation using any peracid such as m-chloroperbenzoic acid; however, this is preferably performed in the presence of bicarbonate. Further reaction with an aryl selenide such as phenyl selenide and a trialklychlorosilane or trifluorosulfonate followed by elimination across the 3,4-position results in an O-alkyl substitution at the 3-position which corresponds to the 13-position in the final product.

Other aspects of the invention include derivatives and analogs of the tetrahydroquinoline diynene core analogs of dynemicin. N-substituted derivatives of the C-13 O-methoxy enediyne, for example, are readily prepared from appropriately substituted chloroformates reacted with 6-methoxy O-protected 3-hydroxyquinoline and the appropriate magnesioacetylide as previously described. The N-substituted compounds include a wide range of alkyl, aryl, benzyl, phenyl, heteroalkyl and aromatic substituents. Carbamate formation is well-studied and extensively used. References are available to practitioners which contain extensive lists of N-substituents with commonly used procedures for synthesis (Green, 1989).

Bridgehead analogs and derivatives of the diynene core are a particularly important group of compounds that may be readily synthesized. The inventors have discovered that the tetrahydroquinoline diynene compounds readily enolize at the bridgehead position, thereby providing a route to substitution at the bridgehead position. Substitution is readily accomplished by treating the diynene in the presence of a base with any of a number of electrophiles; for example, selenides, sulfonates, phosphonates, a-halo ethers and the like. Alternatively, electrophiles substituted at this position may be replaced with other groups; for example, by forming an aryl selenide which is displaced with an alkyl halide.

Other aspects of the invention include the use of the disclosed dynemicin derivatives and analogs as pharmaceutical agents. The parent compound, dynemicin, is a natural product known for its extraordinary potent antimicrobial and antitumor activities with relatively little in vivo toxicity. Acetate derivatives of dynemicin have shown even more activity than the parent compound (Konishi et al., 1989). Now, for the first time, the inventors have described a process for making a core analog of dynemicin. This provides a route to the preparation of several compounds that show activity against solid tumors in vivo.

The active compounds may be administered parentally or intraperitoneally. Solutions of the active compounds as the free base or pharmacologically acceptable salts can be prepared in water suitably mixed with a surfactant such as hydroxypropyl cellulose. Dispersions can also be prepared in glycerol, liquid polyethylene glycol and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be conserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it would be preferable to use isotonic agents, for example, sugars or sodium chloride. Prolonged absorption of the, injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization, for example, by filtration sterilization. Generally, dispersions are prepared by incorporating the various sterilized active ingredients into a sterile vehicle which contains the basic dispersion medium and required other ingredients from those enumerated above. In the case of sterile powders for the preparation of sterile injectable solutions, the preferred methods of preparation are vacuum drying and freeze drying techniques which yield a powder of the active ingredient plus any additional desired ingredient from a previously sterile filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active preparations is well known in the art. Except insofar as any conventional media or agent is incompatible with the active ingredient, its use in the therapeutic compositions is contemplated. Supplementary active ingredients can also be incorporated into the compositions. Additionally, "pharmaceutically acceptable" refers to molecular entities and compositions that do not produce an allergic or similar untoward reaction when administered to a mammal.

It is contemplated that many of the derivatives and analogs of the dynemicin core compounds can be formulated into a composition in a neutral or salt form. Pharmaceutically acceptable salts include the acid addition salts (formed with the free amino group of the molecule) which are formed with inorganic acids such as, for example, hydrochloric or phosphoric acids, or organic acids such as acetic, oxalic, tartaric, mandelic, and the like.

Upon formulation, solutions will be administered in a manner compatible with the dosage formulation and in such an amount as is therapeutically effective. The formulations are easily administered in a variety of dosage forms, such as injectable solutions, drug release capsules, and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, a dosage could be dissolved in one mL of isotonic NaCl solution and either added to 1,000 mL of hypodermic fluid or injected into the proposed site of infusion (see, for example, Remington's Pharmaceutical Sciences, 15th Edition, pp. 1035–1038, and pp. 1570–1580). Some variation in dosage will necessarily occur, depending on the condition of the subject being treated. The person responsible for administration will in any event determine the appropriate dose for the individual subject.

The present invention has provided new approaches and routes to the class of natural products based upon the Z-enediyne functionality. For the first time, the stable free amine of the dynemicin core molecule has been synthesized. The method provides a convenient route to propargylic cation-type intermediates by making use of the $\eta^2$ dicobalt hexacarbonyl alkyne complexes which may be trapped by a wide variety of carbon nucleophiles. The methods disclosed herein are applicable to the synthesis of the core structures of neocarzinostatin as well as dynemicin.

DETAILED DESCRIPTION OF PREFERRED EMBODIMENTS

Dynemicin 1 (R=H) is the latest antitumor antibiotic to be added to the growing list of diynene natural products. It exhibits extraordinary potent antimicrobial and antitumor activity, and moreover it shows relatively little in vivo toxicity. The derived triacetate 2 (R=OAc) is even more hnpressive.

Figure 2:
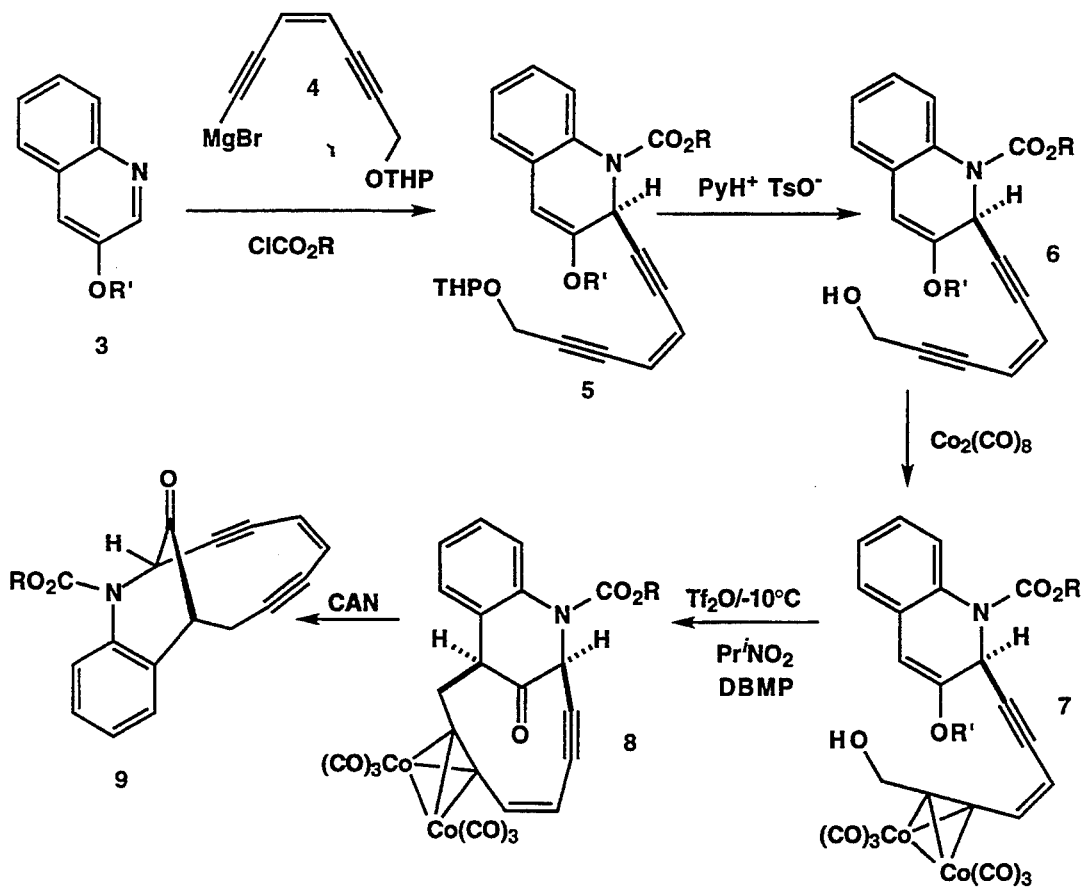
FIG. 2 is a scheme showing the synthesis of the core tetrahydroquinoline diynene portion of esperamicin.

The synthesis of the core tetrahydroquinoline diynene structure 9 using $\eta^2$-dicobalthexacarbonyl acetylene complexes is shown schematically in FIG. 2. The synthesis utilizes simple starting materials and porvides a route to a wide range of diynene derivatives.

Treatment of the t-butyldimethylsilyl ether of 3-hydroxyquinoline 3 with the magnesioacetylide 4 in the presence of a variety of chloroformates gave, in a completely regiospecific reaction, the dihydroquinoline 5[R=Me (86%), R=CH$_2$CH$_2$Cl (71%, R=adamantyl (63 %)]. Selective deprotection of the THP ether to give 6[R=Me (87%), R=CH$_2$CH$_2$Cl (64%), R=adamantyl (74%)] was accomplished using the Grieco procedure (pyridinium tosylate/EtOH) (Miyashita, et at., 1977).

Complexation of 6 with Co$_2$(CO)$_8$ gave 7 [R=Me (47%) R=CH$_2$CH$_2$Cl (56%) R=adamantyl (60%)] along with some complexation at the other acetylene (ca. 15%) and biscomplexation. The desired regioisomer can be separated from the other regioisomer by chromatography. The undesired regioisomer can be oxidized with ceric ammonium nitrate (CAN) to give 6, which can be recycled.

Treatment of 7 with triflic anhydride/[2,6-di-t-butyl-4-methylpyridine (DBMP)] in Pr$^i$NO$_2$ at $-10°$ C. gave the cyclized product 8 (54%). Oxidative decomplexation of 8 using CAN/acetone/$-10°$ C. gave 9 (42%). The overall yield of 9 from 7 for the different carbamates is as follows [R=Me (23%, R=CH$_2$CH$_2$Cl (24%), R=adamantyl (60%)].

Figure 3:
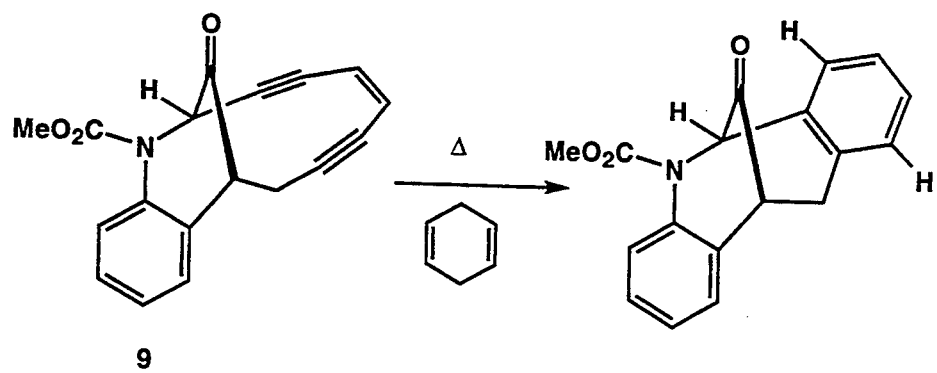
FIG. 3 shows the conversion of azobicyclo[7.3.1]enediyne to the ring-closed azabicyclo benzodiyne compound.

The dynemicin core azobicyclo[7.3.1]diynene 9 proved to be remarkably resistant to cycloaromatization. It required heating in 1,4-cyclohexadiene at 124° C. for hours to convert it into 10 (84%), giving an approximate $\Delta G\{30.9$ kcal mol$^{-1}$ (FIG. 3).

Figure 4:
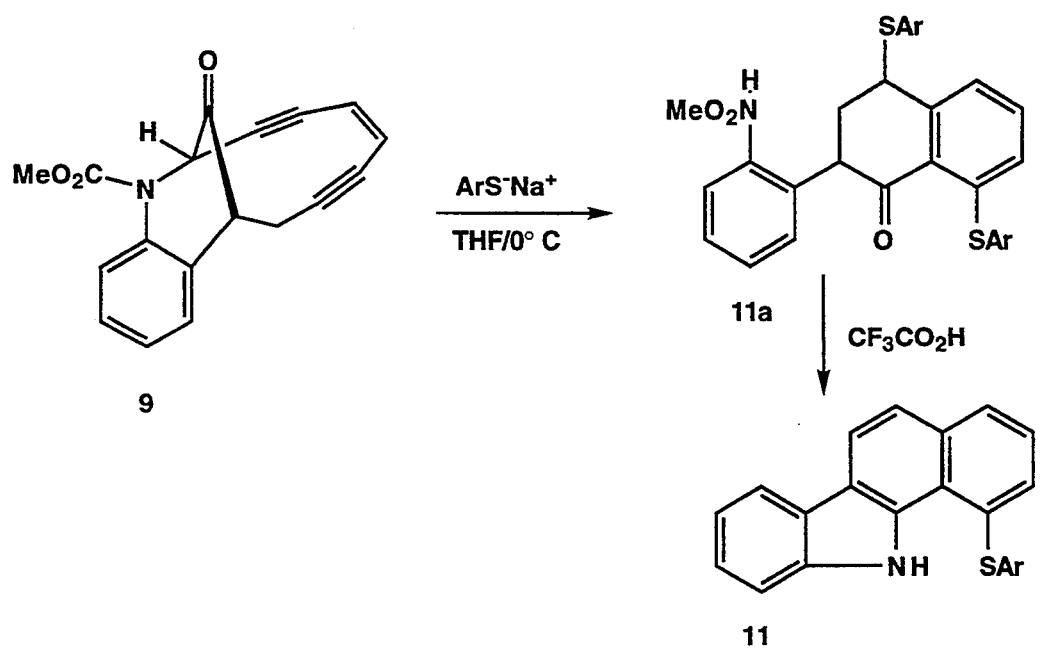
FIG. 4 shows the naphthalene product resulting from treatment of azabicyclo [7.3.1]diynene with sodium thiophenolate at 0° C. in tetrahydrofuran.

The adamantyl carbamate protecting group was chosen with the expectation that it should be readily removed under acidic conditions. Carbamates that require basic or nucleophilic conditions for their removal are precluded since, for example, treatment of 9 with sodium thiophenolate in tetrahydrofuran at 0° C. rapidly gave the: completely aromatized adduct 11 (FIG. 4). The position of the thiophenyl group is uncertain, but the compound is definitely a naphthalene derivative. Further treatment of 9 with trifluoroacetic acid gave compound 11a, as deduced from x-ray crystallography.

Figure 5:
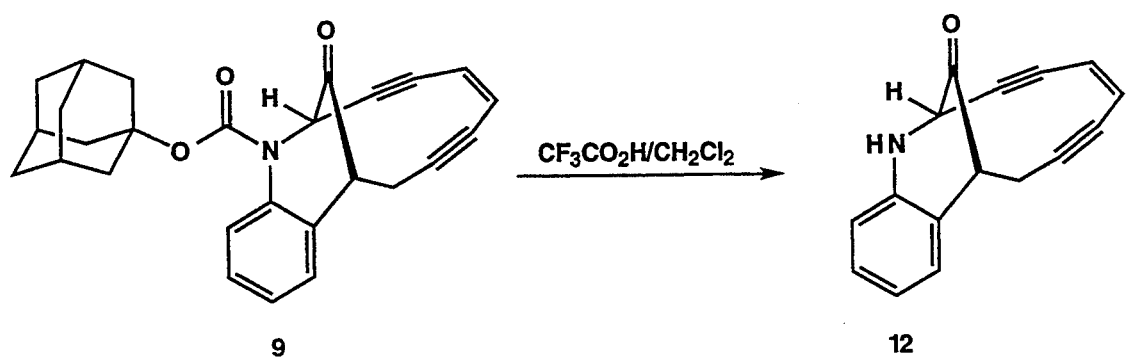
FIG. 5 illustrates the removal of the adamantyl N-protecting group from the azabenzobicyclo[7.3.1]tridec-3,7-diyn-5-ene at room temperature with trifluoroacetic acid in dichloromethane to yield the deprotected amine.

It was found that treatment of the adamantyl carbamate 9 (R=adamantyl) with trifluoroacetic acid in dichloromethane at room temperature gave the deprotected amine 12 in 81% yield (FIG. 5). Starting with 3-(tert-butyldimethylsilyloxy)-6-methoxyquinoline, the same sequence of transformations to make the methoxy analogue of 12 was carried out.

Figure 6:
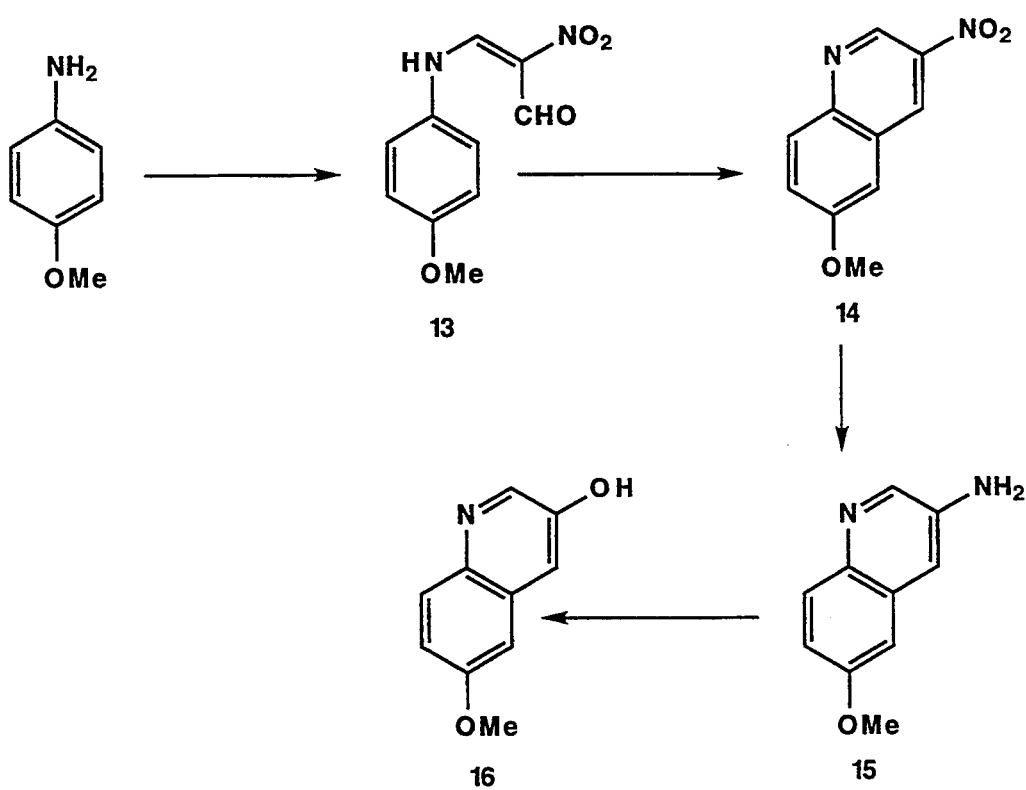
FIG. 6 is a scheme showing the synthesis of 3-hydroxy-6-methoxyquinoline.

3-Hydroxy-6-methoxyquinoline is not, a known compound, and the common methods for synthesizing quinolines are not readily applicable to 3-hydroxy substituents. p-Anisidine hydrochloride was treated with sodium nitromalonaldehyde to give the enamine 13. Heating the enamine 13 in a mixture of acetic acid sulfolane gave 3-nitro-6-methoxyquinoline 14 (30%). The yield of 14 could be improved to 48%, by heating p-anisidine hydrochloride and the enamine 13 in acetic acid in the presence of a catalylic amount of 3,5dimethylthiophenol. Reduction of 14 using stannous chloride gave 3-amino-6methoxyquinoline 15 (86%). Standard diazotization conditions and hydrolysis gave the phenol 16 (95%). Treatment of 16 with t-butyldimethylsilyl chloride/imidazole/in dimethylformamide gave 17 (91%) (FIG. 6).

Figure 7:
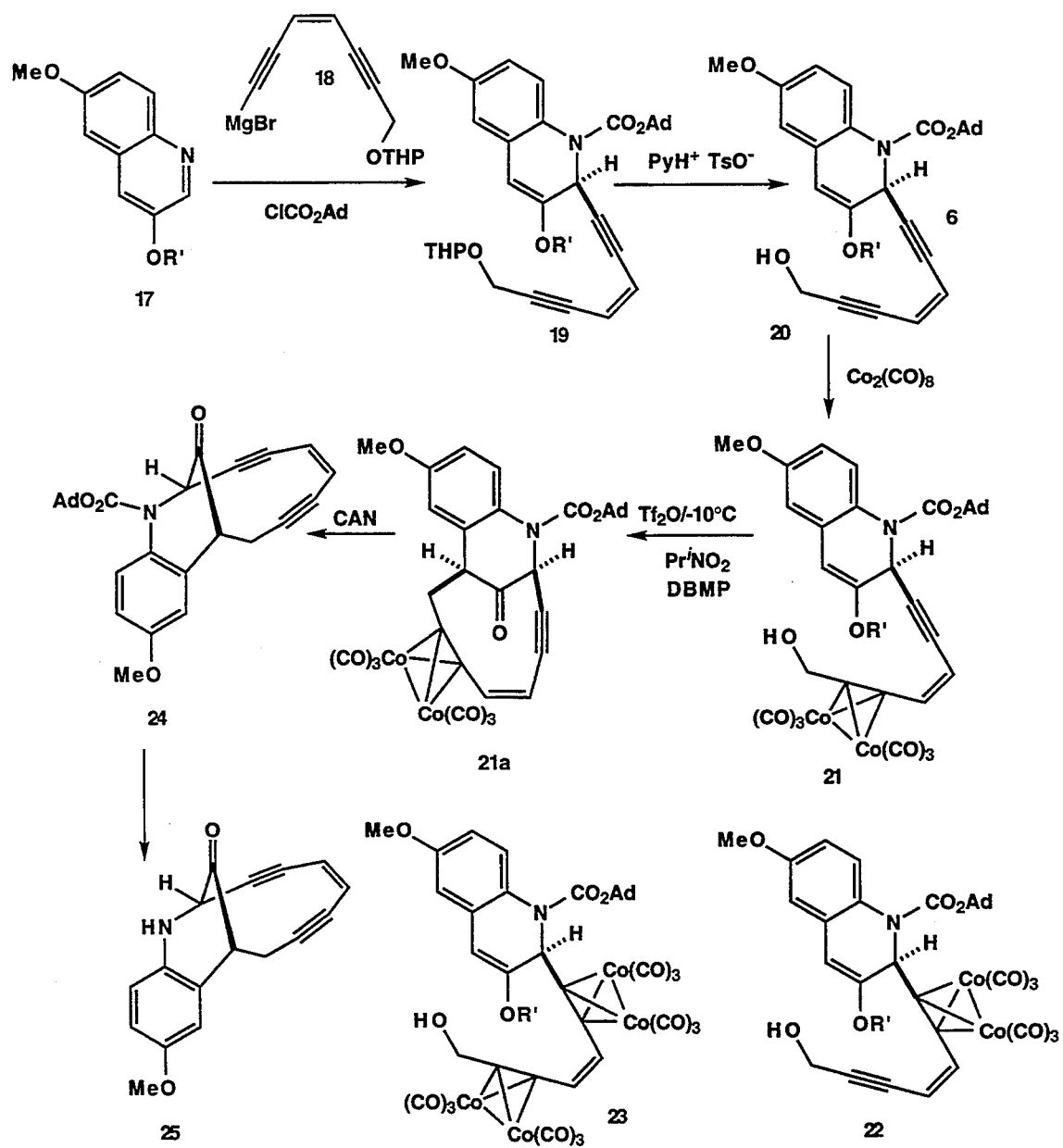
FIG. 7 schematically illustrates the synthesis of the core tetrahydroquinoline diynene moiety of dynemicin.

FIG. 7 shows conversion of 17 to 25. The quinoline 17 was coupled to 18 in the presence of adamantyl chloroformate to give 19 (75%). Hydrolysis of the tetrahydropyranyl ether 19 with pyridinium tosylate gave the alcohol 20 (89%). Complexation of 20 with dicobaltoctacarbonyl in tetrahydrofuran gave 21 (59%), 23 (traces) and 22 (33%). The undesired regioisomer 22 can be recycled by ceric ammonium nitrate oxidation to give 20 (76%).

Treatment of the cobalt adduct 21 with triflic anhydride/2-nitropropane/2,6-di-tert-butyl-4-methylpyridine at $-10°$ C. for 30 min. gave 21a. Direct oxidative work-up by ceric ammonium nitrate oxidation gave the cyclized enediyne 24 (53%, for the two steps.) The adamantyl carbamate was removed by treatment of 24 with trifluoroacetic acid in dichloromethane to give the amine 25 (78%).

EXAMPLE 1

Figure 8:
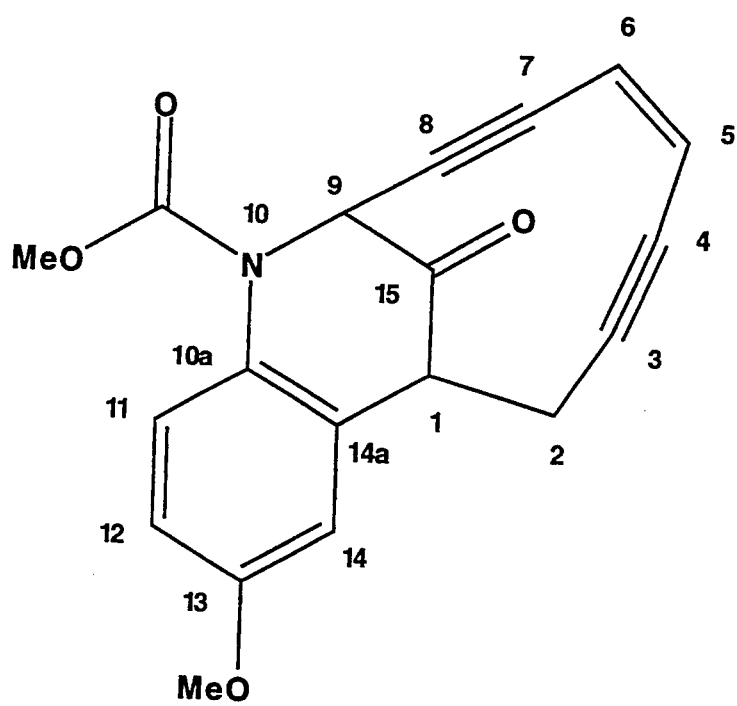
FIG. 8 indicates the numbering system for structures with the azabicyclo[7.3.1]diynene system.

The detailed experimental procedures for the synthesis of the N-[(methoxy)carbonyl]-15-keto-10-aza-14a,10a-benzobicyclo (7.3.1) tridec-3,7-diyn-5-ene and the 13-methoxy analog are described below. The numbering system for the enediyne is shown in FIG. 8. General method for the synthesis of 5 (R—Me, R=CH$_2$CH$_2$Cl, and R=adamantyl).

Ethylmagnesium bromide (23.0 ml 1 M, 0 023 mol) was added to a cooled solution of Z-hept-4-ene-2,6-diyn-1-ol tetrahydropyranyl either 3.63 g (0.019 mol) in 30 ml of THF, stirred for 20 minutes followed by addition of 3-tert-butyldimethylsilyl(oxy) quinoline 4.46 g (0.017 mol) in 20 ml of THF. The chloroformate (2.66 ml, 0.034 mol) was then slowly added over a period of 2 hrs and the mixture to stirred overnight. The reaction mixture was poured onto saturated aqueous NH$_4$Cl, the layers separated and the aqueous layer extracted with diethyl either (3×100 ml). The organic layers were dried (MgSO$_4$) and concentrated in vacuo. The crude product was chromatographed over silica gel eluting with 5% ether/pentane to give the product 5 (5.92 g, 68%).

5 [R=Me (86% yield)].

R<sub>f</sub> 0.22 (95:5-pentane: ether); ¹H NMR (300 MHz, CDCl₃) δ 7.56 (bs, 1H), 7.18–6.98 (m, 3H), 5.80–5.63 (m, 4H), 4.77 (s, 1H), 4.37–4.21 (m, 4H), 3.82 (s, 3H), 3.56–3.52 (m, 2H), 1.89–1.51 (m, 6H), 0.97 (s, 9H), 0.26 (s, 6H); ¹³C NMR (75 MHz, CDCl₃) δ153.9, 150.5, 130.9, 127.7, 125.2, 125.0, 124.5, 123.9, 119.7, 118.9, 116.2, 104.8, 96.6, 93.0, 92.5, 82.6, 80.5, 65.7, 61.8, 54.5, 53.3, 49.2, 30.2, 25.4, 19.0, −4.4, −4.6; IR (CHCl₃) 3041, 3948, 2196, 1713, 1485, 1310, 1022 cm⁻¹; MS (EI+) m/e calcd for C₂₉H₃₇NO₅Si: 507.2441, found 507.2405; Base 318, Parent 5.08.

5 [R=CH₂CH₂Cl (71% yield)]

R<sub>f</sub> 0.33 (10% ether:pentane); ¹H NMR (300 MHz, CDCl₃) δ7.62 (bs, 1H), 7.17–6.95 (m, 3H), 5.80–5.66 (m, 4H), 4.79 (s, 1H), 4.60–4.23 (m, 4H), 3.89–3.62 (m, 3H0, 3.59–3.44 (m, 1H), 2.83–2.51 (m, 6H), 0.97 (s, 9H), 0.29 (s, 3H), 0.27 (s, 3H); ¹³C NMR (75 MHz, CDCl₃) δ153.0, 131.2, 128.2, 125,3, 125.3, 125.0, 124.9, 119.9, 1.18.9, 103.1, 96.8, 93.1, 82.6, 80.6, 67.4, 65.9, 61.9, 54.6, 49.3, 41.6, 41.0, 30.2, 25.6, 25.5, 25.3, 19.0, 18.1, 15.2, −4.4, −4.8.

5 [R=adamantyl (64% yield)].

R<sub>f</sub> 0.21 (95:5-pentane: ether); ¹H NMR (300 MHz, CDCl₃) δ7.56–7.55 (bm, 1H), 7.09–6.97 (m, 3H), 5.76–5.68 (m, 4H), 4.75 (bs, 1H), 4.35–4.19 (q, 2H), 3.87 (m, 1H), 3.57 (M, 1H), 2.17 (s, 9H), 1.83–1.52 (m, 12H), .97 (s, 9H), .26 (s, 3H), 0.25 (s, 3H); ¹³C NMR (75 MHz, CDCl₃) δ151.9, 150.1, 131.6, 129.0, 127.7, 126.9, 125.2, 124.9, 1.24.8, 124.3, 119.5, 119.3, 103.5, 96.9, 93.1, 92.9, 82.7, 81.9, 80.2, 61.9, 54.7, 48.9, 41.5, 36.2, 31.0, 30.1, 25.6, 19.1 −4.4, −4.7; IR (CDCl₃) 2973, 2956, 2196, 1702, 1655, 1489, 1244 cm⁻¹; MS (CI +) m/e calc'd for C₃₈H₄₉NO₅Si: 627.3380, found 627.3389; Base 544, Parent 628.

Removal of the Tetrahydropyranyl Protecting group from 5 to give 6.

A solution of the THP protected adduct 5 1.34 g (2.64 mmol) and TsOH·H₂O 0.15 g in ethanol (30 ml) was stirred at 55° C. overnight. The mixture was concentrated in vacuo, redissolved in ether, washed with aqueous sodium bicarbonate, brine, dried (MgSO₄) and filtered. The filtrate was concentrated in vacuo and chromatographed over silica gel eluting with 40% ether/pentane to give the deprotected alcohol 6 (0.976 g, 87%).

6 [R=Me (84% yield)].

M.p. 101°–102° C.; ¹H NMR (300 MHz, CDCl₃ δ7.58 (bs, 1H), 7.11–7.02 (s, 3H), 5.79 (bs, 1H), 5.78–5.70 (m, 2H), 5.68 (s, 1H), 4.26 (s, 2H), 3.82 (s, 3H), 2.19 (bs, 1H) 0.98 (s, 9H), 0.28 (s, 3H), 0.27 (s, 3H); ¹³C NMR (75 MHz, CDCl₃) δ154.3, 150.4, 130.9, 127.7, 125.3, 125.2, 124.7, 123.7, 120.1, 119.2, 103.0, 95.4, 92.6, 82.4, 80.6, 53.4, 51.2, 49.3, 24.4, 18.0, −4.40, −4.83; IR (CHCl₃) 3449, 3051, 2965, 2930, 2896, 2997, 2205, 1704, 1656, 1570, 1492, 1462, 1436, 1371, 1327, 1306, 1250, 1172, 1025 cm⁻¹; MS m/e calc'd for C₂₄H₂₉NO₄Si: 423.1866, found 423.1883.

6 [R=CH₂CH₂Cl (64% yield)].

R<sub>f</sub> 0.31 (50:50-ether:pentane); ¹H NMR (300 MHz, CDCl₃ δ7.64–7.62 (bs, 1H), 7.16–7.00 (m, 3H), 5.79–5.70 (m, 4H), 4.58–4.52 (m, 1H), 4.42–4.36 (m, 1H), 4.26 (s, 2H), 3.77–3.69 (m, 2H), 0.97 (s, 9H), 0.27 (s, 3H), 0.26 (s, 3H); ¹³C NMR (75 MHz, CDCl₃) δ154.3, 127.8, 125.3, 125.0, 124.0, 120.2, 119.4, 103.2, 5.3, 82.6, 66.1, 66.0, 65.9, 51.4, 49.4, 41.7, 25.5, 18.1, 15.3, −4.3, −4.7; IR (CHCl₃) 3495, 3017, 2957, 2058, 1701, 1654, 1174 cm⁻¹; MS (CI+) m/e calc'd for C₂₅H₃₀NO₄SiCl: 471.1632, found 471.1616; base 366, parent 472.

6 [R=adamantyl (78% yield)].

R<sub>f</sub> 0.36 (50:50-ether:pentane); ¹H NMR (300 MHz, CDCl=l₃) δ7.58 (bs, 1H), 7.11–6.98 (m, 3H), 5.78–5.69 (m, 3H), 4.25 (s, 2H), 2.61 (s, 9H), 2.17 (s, 6H), 0.97 (s 3H), 0.26 (s, 3H); ¹³C NMR (75 MHz, CDCl₃) δ168.2, 131.6, 127.7, 125.3, 124.3, 119.9, 119.8, 119.0, 103.5, 95.2, 93.2, 82.6, 82.2, 80.3, 51.4, 48.9, 41.5, 36.1, 30.9, 25.6, 18.2, −4.4, −4.67; IR (CHCl₃) 3460, 2918, 1689, 1489, 1335, 1247, 1050 cm⁻¹; MS m/e calc'd for C₃₃H₄₂NO₄Si: 544,2883, found 544.2876.

Complexation of 6 with dicobaltoctacarbonyl to give 7.

A 100 ml round bottom flask was charged with alcohol 6 (1.0 g, 2.36 mmol) and 50 ml of ethyl acetate. The mixture was cooled to 0° C. followed by the: rapid addition of Co₂(CO)₈ (0.89 g, 1.1 eq) as a solid. Immediate evolution of gas was observed. The mixture was stirred for 15 minutes and then concentrated to dryness. The crude product was chromatographed over silica (200 times the original weight of starting material) and eluted with 20% ether/pentane.

7 [R=Me (47% yield) }.

¹H NMR (300 MHz, CDCl₃) δ7.90 (bs, 1H), 7.02 (6.96, J=m Hz, 1H), 6.88–6.81 (m, 2H), 6.23 (bs, 1H), 6.11 (d, J=10.6 Hz, 1H), 5.17 (dd, J=10.6, 2.3 Hz, 1H), 4.87 (q, J =18.2, 5.4 Hz, 2H), 3.36 (s, 3H), 1.93 (bs, 1H), 0.95 (s, 9H), 0.18 (s, 3H), 0.16 (s, 3H); ¹³C NMR (75 MHz, CDCl₃) δ199.4–198.7, 154.2, 150, 138.3, 130.9, 127.7, 125.6, 125.5, 125.0, 123.9, 109.8, 103.2, 97.5, 95.3, 81.6, 81.5, 64.08, 53.6, 49.6, 25.5, 18.2, −4.35, 4.73; −4.73; IR (CHCl₃) 2957, 2930, 2865, 2093, 2085, 2031, 1702, 1660, 1557, 1523, 1441, 1377, 1313, 1255, 1178, 1026, 834 cm⁻¹; MS m/e calc'd for C₃₀H₂₉NO₁₀SiCo₂ (M+-OH): 693.0276, found 693.0341.

7 [R=CH₂CH₂Cl (56% yield)].

R<sub>f</sub> 37 (80:20-pemane:ether); ¹H NMR (75 MHz, CDCl₃) 6 7.63 (bs, 1H), 7.18–7.02 (m, 3H), 6.69 (d, J=9.15 Hz, 1H), 5.82 (s, 1H), 5.73 (s, 1H), 5.61 (d, J=9.4 Hz, 1H), 4.80–4.52 (m, 4H), 4.41 (bs, 1H), 3.79 (bs, 2H), 1.99 (s, 9H), 0.27 (s, 3H), ¹³C NMR (300 MHz, CDCl₃)δ1990.198-0, 152.7, 138.4, 127.8, 125.6, 125.5, 125.2, 125.1, 109.7, 103.3, 100.9, 99.9, 95.0, 81.7, 66.1, 66.0, 49.9, 41.7, 29.2, 25.5, 18.1, 16.4, −4.3, −4.7.

7 [R=adamamyl (60% yield)].

R<sub>f</sub> 30 (80:20-pemane:ether); ¹H NMR (300 MHz, CDCl₃) δ7.61–7.54 (bd, 1H), 7.19–7.02 (m, 3H), 6.71 (d, J=9.2 Hz, 1H), 5.83 (s, 1H), 5.76 (s, 1H), 5.63 (dd, J=9.2, 2.3 Hz, 1H), 4.82–4.60 (m, 2H), 2.17 (s, 9H), 1.72 (s, 6H), 0.97 (s, 9H), 0.27 (s, 3H); ¹³C NMR (75 MHz, CDCl₃)δ199.0–198.8, 151.9, 149.9, 138.2, 131.4, 127.6, 125.5, 125.1, 124.4, 124.3, 110.0, 103.6, 97.6, 95.9, 82.3, 81.7, 81.3, 64.1, 49.0, 41.4, 36.1, 20.9, (25.5), 18.1, −4.4, −4.7; IR (CHCl₃) 3215, 2863, 2605, 2030, 1963, 1490, 1297 cm⁻¹; MS (FAB-) m/e Base 171, parent 828.

General Procedure for the Cyclization of 7 to give 8.

To a cooled mixture of 1-nitropropane (20 ml), cobalt complexed alcohol 7 (0.80 g, 1.06 retool) and 2,6-di-t-butyl-4-methylpyridine (DBMP) (1.29 g, 6.30 mmol) was rapidly added triflic anhydride (Tf₂O) (0.54 ml, 3.18 mmol). The mixture was stirred at −10° C. for 15 min followed by the addition of NaHCO₃ (sat), the layers were separated, and the aqueous layer extraction with diethyl ether (3×25 ml), dried [MgSO₄]. The organic layer was filtered and concentrated in vacuo followed by chromatography over a silica gel column eluting with 20% ether:pentane to give the product 8 (0.333 g, 545/0).

8 [R=Me (54% yield)].

R_f 30 (20:80 ether:pemane); $^1$H NMR (300 MHz, CDCl$_3$) δ7.65 (d, J=8.15 Hz, 1H), 7.36–7.30 (m, 1H), 7.23–7.17 (m, 2H), 6.92 (d, J=9.8 Hz, 1H), 5.63 (dd, J=9.8, 2.5 Hz, 1H), 5.12 (d, J=0.9 Hz, 1H), 4.53–4.44 (AB, J=11.2 Hz, 1H), 3.93 (s, 3H), 3.88–3.8 (dd, J=11.2, 4.12 Hz, 1H), 3.60–3.53 (dd, J=15.3, 4.1 Hz, 1H); $^{13}$C NMR (75 MHz, CDCl$_3$) δ199.0–198.8, 193.7, 153.6, 143.7, 136.2, 128.9, 128.3, 127.2, 125.9, 123.4, 108.8, 92.3, 92.0, 90.6, 81.7, 56.6, 54.9, 53.6, 40.2; IR (CHCl$_3$) 2943, 2919, 2848, 2896, 2061, 2038, 2026, 1713, 1601, 1484, 1454, 1437, 1372, 1343, 1320, 1290, 1261, 1243, 1155, 1055, 908 cm$^{-1}$; MS m/e calc'd for C$_{22}$H$_{13}$NO$_7$Co$_2$ (M+-2CO): 520.9365, found 520.9356.

General Procedure for Oxidative Decomplexation of 8 to give 9.

To a cooled (−10° C.) mixture of acetone (10 ml) and cobalt-complex 8 0.0756 g (0.130 mmol) was added in three portions (over 3 minutes) ceric ammonium nitrate (CAN) (0.214 g, 0.039 mmol). The mixture was stirred for an additional 15 minutes, with rapid evolution of gas occurring. The crude mixture was poured onto a fritted filter with silica (10 g) and celite 454® (5.0 g) eluting with 200 ml of ether. The ether layers were concentrated and the crude product chromatographed over silica gel eluting with 50% ether:pentane to give the product 9 (016 g, 42% ).

9 [R=Me (42% yield)].

M.p. Decomposes at 150° C.; $^1$H NMR (300 MHz, CDCl$_3$)δ7.56 (d, J=7.6 Hz, 1H), 7.35–7.26 (m, 3H), 5.88 (s, 1H), 5.79–5.62 (AB, 9.5 Hz, 2H), 3.84 (s, 3H), 3.75–3.72 (m, 1H), 3.55–3.45 (m, 1H), 3.34–3.26 (m, 1H); $^{13}$C NMR (75 MHz, CDCl$_3$) δ198.4, 153.9, 135.7, 128.4, 127.5, 126.5, 126.3, 126.1, 125.7, 121.2, 99.3, 91.8, 89.2, 82.6, 54.4, 53.07, 49.2, 21.6; IR (CHCl$_3$) 3032, 3011, 2958, 2928, 2855, 2207, 1737, 1711, 1583, 1494, 1459, 14.43, 1371, 1323, 1293, 1247, 1195, 1160, 1137, 1118, 1098, 1058, 1042, 1027, 979 cm$^{-1}$; MS m/e calc'd for C$_{18}$H$_{13}$NO$_3$ (M+): 291.0895, found 291.0888.

General One Pot Procedure for Converting 7 into 9.

To a cooled mixture of 2-nitropropane (39.0 ml), cobalt complexed alcohol 7 (0.913 g, 1.10 mmol) and 2,6-di-t-butyl-4-methylpyridine (DBMP) (1.13 g, 5.50 mmol) was rapidly added triflic anhydride (Tf$_2$O) (0.56 ml, 3.30 mmol). The mixture was stirred at −10° C. for 15 min followed by the addition of NaHCO$_3$ (sat), the layers were separated, and the aqueous layer extracted with 2-nitropropane (3×10 ml) and dried (MgSO$_4$). The organic layers were filtered and diluted with an additional 70 ml of acetone, cooled to −10° C., followed by the addition of ceric ammonium nitrate (CAN) (4.82 g, 8.80 mmol) in three portions (over 5 minutes). The reaction was stirred for an additional 15 minutes with rapid evolution of gas occurring, the addition of Hunig's base 4.80 ml (27.5 mmol) resulted in the formation of a brown precipitate. The crude reaction mixture was poured onto a frit of silica (50 g) and eluted with ethyl acetate (500 ml). The organic layers were concentrated and the crude product chromatographed over silica gel eluting with dichloromethane to give the product 9 (0.247 g, 55%).

9 [R=CH$_2$CH$_2$Cl (24% yield)].

R_f 62 (50:50-ether:pemane); $^1$H NMR (300 MHz, CDCl$_3$) δ7.59 (d, 1H), 7.36–7.25 (m, 3H), 5.88 (s, 1H), 5.79–5.76 (d, J=9.46 Hz, 1H), 5.64–5.61 (d, J=9.72 Hz, 1H), 4.39 (m, 1H), 3.78 (m, 2H), 3.56 (m, 2H), 3.31–3.23 (m, 1H); $^{13}$C NMR (75 MHz, CDCl$_3$) δ198.1, 153.8, 135.3, 128.3, 127.5, 126.5, 126.3, 126.2, 125.7, 121.1, 99.2, 91.9, 88.9, 83.3, 66.2, 54.3, 49.1, 41.6, 21.6; IR (CHCl$_3$) 2957, 2927, 2205, 1737, 1711, 1398, 1285 cm$^{-1}$; MS m/e calc'd for C$_{19}$H$_{14}$NO$_3$Cl: 339.0662, found 339.0663.

9 [R=adamantyl (55% yield)].

R_f 46 (50:50-ether:pentane); $^1$H NMR (300 MHz, CDCl$_3$) δ7.55 (d, J=7.31 Hz, 1H), 7.29–7.21 (m, 3H), 5.82 (s, 1H), 5.75 (d, J=9.3 Hz, 1H), 5.63 (d, J=9.6Hz, 1H), 3.71 (bs, 1H), 3.54–3.50 (m, 1H) 3.48–3.20 (dd, J=14.5, 2.97 Hz, 1H), 2.15 (s, 9H), 1.6 $^{13}$C NMR (75 MHz, CDCl$_3$)δ198.9, 151.7, 136.1, 128.2, 127.2, 126.3, 126.2, 125.8, 125.6, 121.2, 99.3, 91.4 89.7, 83.3, 82.7, 49.1, 41.4, 36.2, 36.0, 30.9, 21.5; IR (CHCl$_3$) 3013, 2917, 2341, 1736, 1698, 1364, 1048 cm$^{-1}$; MS (CI+) m/e calc'd for C$_{27}$H$_{25}$NO$_3$: 411.1834, found 411.1825; parent 411, Base 153.

Deprotection of the Adamantyl Carbamate 9 to give 12.

To a solution of carbamate 9 (0.247 g. 0.60 mmol) in 10 ml of dichloromethane, was 2.31 ml (30.0 mmol) of trifluoroacetic and the mixture stirred for 2 hours. The mixture was quenched by the addition of NaHCO$_3$ and extracted with dichloromethane (3×25 ml). The resulting organic extracts were dried over MgSO$_4$, filtered, concentrated in vacuo and chromatographed over silica gel eluting with dichloromethane to give 0.140 g (81% yield) of 12.

12. Rf 0.50 (50:50-ether:pentane); $^1$H NMR (300 MHz, CDCl$_3$) δ7.25–7.22 (d, J=9.67 Hz, 1H), 7.15 (t, J=7.47 Hz, 1H), 6.95 (t, J=7.48 Hz, 1H), 6.74 (d, J=7.87 Hz, 1H), 5.73 (q, J=22.4, 9.11 Hz, 2H), 4.62 (s, 1H), 4.23 (bs, 1H), 3.63 (t, J=4.08 Hz, 1H), 3.51 (dd, J=2.88 Hz, 1H), 3.39 (qd, J=17.72, 4.78, 1.70 Hz, 1H); $^{13}$C NMR (75 MHz, CDCl$_3$) δ199.6, 142.4, 127.9, 126.6, 125.8, 122.3, 121.3, 120.9, 116.5, 100.1, 92.7, 90.0, 83.0, 54.0, 53.4, 21.7; IR (CH$_2$Cl$_2$) 3379, 2986, 2305, 1733, 1422, 1265, 896 cm$^{-1}$; MS m/e calc'd for C$_{16}$H$_2$NO: 233.0840, found 233.0834.

6-Methoxy-3-nitroquinoline 14.

p-Anisidine hydrochloride (35.0 g, 219.4 mmol) was weighed into a dry 300 mL three-necked round-bottomed flask, equipped with a magnetic stirring bar, a pressure-equalizing addition funnel, a solid addition funnel and a thermometer. Glacial acetic acid (150 mL) was added to the solid, with vigorous stirring to maintain a homogeneous suspension. To this suspension was added sodium nitromalonaldehyde monohydrate (12.0 g, 76.4 mmol) and the mixture stirred for 1.0 h at 25° C. A short-path distillation head was placed on the flask and approximately 120 mL of acetic acid/water removed under reduced pressure at 40° C. To the residue (imine 13) was added glacial acetic acid (40 mL) and sulfolane (75 mL). The resulting solution was flushed with argon to :remove air and the flask immersed in an oil bath preheated to 195° C. The mixture was vigorously stirred while acetic acid was removed by distillation. When the temperature reached 184°–185° C. the mixture was stirred for a further 15 min at 185° C. and then poured (while still at ca. 180° C.) onto crushed ice (750 g). The resulting solution was allowed to stand in a refrigerator (overnight) until precipitation was complete. The dark brown solid precipitate was filtered and transferred to a round-bottomed flask (500 mL) containing 2M hydrochloric acid (250 mL). The mixture was heated at reflux for 50–60 min and the boiling; solution filtered through a preheated Büchner funnel to remove an insoluble brown gum. The hot filtrate was cooled to ca. 4° C. and extracted with chloroform (4×50 mL). The combined extracts were dried (MgSO$_4$) and the chloroform removed on a rotatory evaporator to give the crude 3-nitro-6-methoxyquinoline 14 (9.3 g, brown solid).

The crude quinoline was dissolved in boiling 95% ethanol (ca. 125 mL) and the hot solution was carefully treated with decolorizing carbon (ca. 3.0 g). The hot solution was then filtered through a cake of celite, which was then washed with boiling ethanol (5.10 mL). The hot solution was allowed to cool slowly to room temperature and then placed in the freezer overnight. The light brown, fine crystals were filtered off, washed once with chilled ethanol (12 mL) and then dried in a desiccator under high vacuum to give 3-nitro-6-methoxyquinoline 14 (4.72 g, 30.25% yield).

The mother liquor was concentrated and the resulting brown solid (ca. 3.0 g) chromatographed on $SiO_2$ (100 g. flash) with 20% ethyl acetate in hexanes as eluant (chloroform can also be used as eluant). The resulting 1.58 gms of product were recrystallized from 95% ethanol (as above) yielding 0.91 gms of product (5.83% yield). Overall yield based on sodium nitromalonaldehyde monohydrate was 36.08%. 14. M.p. 133°–135° C.; $^1$H NMR (300 MHz, $CDCl_3$) δ9.5 (d, J=2.4 Hz, 1H), 8.92 (d, J=2.4 Hz, 1H), (d, J=9.1 Hz, 1H), 7.57 (dd, J=2.7 9.1 Hz, 1H), 7.24 (d, J=2.7, Hz, 1H 3.99 (s, 1H); $^{13}$C NMR (75 MHz, $CDCl_3$) δ159.3, 146.4, 141.4, 141.3, 131.0, 130.5, 127.4, 126.4, 106.3, 55.8; IR ($CHCl_3$) 3075, 3015, 2965, 2940, 1624, 1612, 1577, 1543, 1500, 1466, 1428, 1378, 1360, 1232, 1029 $cm^{-1}$; MS (CI) m/e calculated for $C_{10}H_9N_2O_3$: 205.061, found 205.0613, base peak 205, parent peak 205, 188, 158, 154; Anal calcd for $C_{10}H_8N_2O_3$: C, 58.82%; H, 3.95%; N, 13.72%; Found: C, 58.78%; H, 3.87%; N, 13.50%.

Alternative Procedure.

A 250 ml 3-neck round bottom flask (equipped with condenser/argon inlet, magnetic stirrer and thermometer) was charged with the enamine 13 (8.0 g, 36.0 mmoles) and p-anisidine hydrochloride (11.48 g, 72.mmoles) and glacial acetic acid (72 mL) added. The flask was purged with a stream of argon and the mixture was stirred and heated to reflux (ca. 116° C.). The suspension became a dark brown solution at ca. 90° C. The solution was heated at reflux for approximately 80 min. A catalytic amount of 3,5-dimethylthiophenol (0.995 g, 7.2 mmole) was added and the mixture heated at reflux for 50 hours. The progress of the reactions can be followed by tlc ($SiO_2$, 20% ethyl acetate in hexanes, three developments).

After 50 hours the reaction mixture was allowed to cool to room temperature and the acetic acid removed by rotary-evaporation under oil pump vacuum (bath at ca. 55° C.). The dark brown residue was heated at reflux with 2M HCl (200 mL) for 30–50 min. The hot aqueous solution was filtered through a Buchner funnel (brown gum—insoluble in hot HCl was discarded after tlc indicates only minimal amount of the product was present) cooled to 4° C. and extracted with chloroform (4×50 mL). The combined organic extracts, were dried ($MgSO_4$) and the solvent removed by rotary evaporation and high vacuum. The crude product was purified by recrystallization from boiling 95% EtOH and column chromatography (20% EtO Ac-hexanes) of the mother liquor concentrate on $SiO_2$. Total yield of purified product 14 was 3.55 g (48.3%).

Preparation of Enamine 13:

p-Anisidine hydrochloride (12.8 gms. 80.0 mmol) was dissolved in 2M HCl (32 mL) and the stirred solution diluted with water (35 mL). To this solution was added, at room temperature, sodium nitromalonaldehyde monohydrate (1) (10.04 gms, 64.0 mmoles) Org. Syn. Col. Vol. IV, 844, ca. 64.0 mmol) dissolved in water (80 mL). A yellow precipitate formed instantaneously and the thick mixture was stirred with a glass rod. After ca. 20 min. at room temperature the precipitate was filtered on a Buchner funnel, the press cake washed with distilled water (1×80 mL), air dried for 3 hours and then suspended in ether as a thick slurry. Filtration, followed by air drying on the Buchner gave the enamine 13, which was further dried over $P_2O_5$ (desiccator under vacuum overnight). Yield: 10.7 to 12.1 gms (7585%).

6-Methoxy-3-aminoquinoline 15

21.2 g (0.104 mole) of the nitroquinoline 14 was added portionwise to a 1.0 L beaker containing 320 mL conc. HCl at 50° C., with vigorous stirring. Then the heating bath was removed and 71.0 g of $SnCl_2 \cdot 2H_2O$ (0.312 mole, finely ground) was added portionwise over 2–3 min (the temperature of the mixture reached 80° C.). The mixture was stirred vigorously for 10 min, and diluted with water to 1.0 L. The pH was adjusted to 9 using 5M NaOH (900–950 mL) and the aqueous layer (2.0 L) was cooled to 4° C., and extracted with EtOAc (3×500 mL). The combined organic layers were washed with ice-cold water (200 mL), brine (400 mL) and dried over anhydrous $MgSO_4$. Filtration and removal of the solvent in vacuo gave 17.6 g of crude 15. The crude product was vigorously stirred with 50 mL $CHCl_3$ and the tan microcrystalline solid forming was filtered on a sintered glass funnel. The precipitate was washed with $CHCl_3$ (2×25 mL) and then air dried. Removal of the last traces of solvent in vacuo gave 8.1 g of product. The washings were combined with the filtrate, concentrated by rotovap and placed in the freezer. Two more crops of 15 were thus obtained (3.8 and 2.3 g). The mother liquor concentrate was purified by column chromatography on silica gel (EtOAc -hexanes 1:1) and a further 1.3 g of product 15 was obtained (overall yield 15.5 g, 86%). A small amount of 4-chloro-6-methoxy-3-aminoquinoline (5%) was also obtained as a less polar byproduct.

15 $^1$H NMR (300 MHz, $CDCl_3$) δ8.33 (d, J=2.7 Hz, 1H), 7.84 (d, J=9.1 Hz, 1H), 7.13 (d, J=2.6 Hz, 1H), 7.10 (dd, J=2.6, 9.1 Hz, 1H), 6.85 (d, J=2.7 Hz, 1H), 3.92 (s, 3H), 3.50 (br, 2H); $^{13}$C NMR (75 MHz, $CDCl_3$) δ158.1, 140.4, 140.1, 138.7, 130.4, 130.2, 118.0, 114.2, 103.6, 55.3; MS (CI) m/e calcd for $C_{10}H_{10}N_2O$: 174.079, Found 174.079; base peak 175, parent peak 175.

3-Hydroxy-6-methoxy quinoline 16.

17.4 g (0.1 mole) of the aniline 15 was dissolved in 335 mL 2N HCl and the mixture was diluted with 280 mL water and cooled to 4° C. Addition of 7.5 g (0.109 mole) $NaNO_2$ in 70 ml water followed by stirring at 4° C. for two hours gave a solution of the diazonium salt 15a. This solution was added to a vigorously stirred solution of 161 mL conc. $H_2SO_4$ and 385 mL water at 85°–90° C. (addition time 1 hour). The resulting solution was stirred at 90°–95° C. for an additional hour, cooled to room temperature, neutralized with solid $NaHCO_3$, cooled to 0° C. and extracted with EtOAc (3×800 mL). The combined organic layers were dried ($MgSO_4$) filtered and the solvent removed in vacuo. The crude 16 thus obtained (16.6 g, 95% yield) was used directly in the next step. 16 $^1$H NMR (300 MHz, DMSO-$d^6$/$CDCl_3$) δ9.60 (br, 1H), 8.36 (d, J=2.6 Hz, 1H), 7.72 (d, J=9.1 Hz, 1H), 7.27 (d, J=2, 6 Hz, 1H), 7.01 (dd, J=2.7, 9.1 Hz, 1H), 6.85 (d, J=2.7 Hz, 1H), 3.80 (s, 3H); $^{13}$C NMR (75 MHz, DMSO-$d^6$) d 157.7, 151.4, 141.1, 138.5, 130.5, 130.0, 118.3, 114.8, 104.5, 55.3; MS (CI)

m/e calcd for $C_{10}H_9NO_2$; 175.063, Found 175.064; base peak 176, parent peak 176, 159, 157, 141, 119.

3-(tert-butyldimethylsilyloxy)-6-methoxyquinoline 17.

A 500 mL flask, equipped with magnetic stirrer and septum, was charged with 16.6 g crude 16 (0.095 mole), 22.1 g TBDMS-Cl (97%, 0.142 mole), 13.1 g imidazole (99%, 0.19 mole) and 240 mL DMF (distilled, added by syringe). The mixture was stirred under argon for 8 hours and then poured into 1.0 L of water and extracted with ether ($3 \times 450$ mL). The combined organic extracts were dried ($MgSO_4$), filtered and the solvent removed in vacuo to give 36.4 g of crude (orange solid). Crystallization from $Et_2O$-pentane (1:9) and chromatography of the mother liquor concentrate on silica gel ($Et_2O$-pentane 1:2) gave 25.0 g of 17, 91% yield.

17 M.p. 59°–61° C.; $^1$H NMR (300 MHz, $CDCl_3$) δ8.40 (d, J=2.5 Hz, 1H), 7.91 (d, J=9.2 Hz, 1H), 7.32 (d, J=2.6 Hz, 1H), 7.20 (dd, J=2.7, 9.2 Hz, 1H), 6.9 (d, J=2.7 Hz, 1H), 3.95 (s, 3H), 1.02 (s, 6H), 0.12 (s, 6H); $^{13}$C NMR (75 MHz, $CDCl_3$) δ158.0, 149.6, 143.9, 139.8, 130.3, 130.1, 120.6, 119.6, 104.2, 55.3, 25.5, 18.3, −4.5; MS (CI)m/e calculated for $C_{16}H_{23}NO_2Si$: 289.149, found 289.150; base peak 290, parent peak 289, 232, 137, 135, 133, 113; Anal calcd for $C_{16}H_{23}NO_2Si$: C, 66.39%; H, 8.01%; N, 4.84%; found: C, 66.17%; H, 8.06%; N, 4.62%.

Coupling quinoline 17 and enediyne 18 to give 19.

A solution of ethylmagnesium bromide in THF (43 ml 1M solution, 43.3 mmol) was added to a solution of z-hept-4-ene-2,6-diyn-1-ol tetrahydropyranyl ether 18 (6.89 g, 36.2 mmol) and 6-methoxy-3-(tert-butyldimethylsiloxy)-quinoline 17 (9.41 g, 32.5 mmol) in THF (210 ml) cooled to 0° C. After the initial evolution of gas the reaction mixture was stirred for 20 minutes at 0° C. and a solution of adamantyl chloroformate (11.51 g, 53.6 mmol) in THF (40 ml) was added via syringe pump over 90 minutes while maintaining the temperature at 0° C. On completion of the addition, the reaction mixture was allowed to warm to room temperature and stirred for 18 hours before quenching with saturated aqueous sodium bicarbonate solution (60 ml). The resulting mixture was extracted with ether ($1 \times 300$ ml, $2 \times 150$ ml), the combined organic extracts dried over magnesium sulphate and evaporated to give a brown oil. Flash column chromatography on silica gel eluting with 80% pentant, 20% diethylether yielded 16.11 g, (75%) of the desired product 19 as a clear yellow oil. $^1$H NMR (300 MHz, $CDCl_3$) δ7.43 (s, 1H), 6.62 (dd, J=8.8, 2.8 Hz, 1H), 6.52 (d, J=2.8 Hz, 1H), 5.74 (dd, J=11.0, 1.4 Hz, 1H), 5.68–5.79 (s, 1H), 5.67 (d, J=11.0 Hz, 1H 5.62 (s, 1H), 4.75 (s, 1H), 4.31 (dd, J=16.0, 1.4 Hz, 1H), 4.23 (dd, J=16.0, 1.4 Hz, 1H), 3.77–3.89 (m, 1H), 3.76 (s, 3H), 3.46–3.58 (m, 1H), 2.15 (s, 9H), 1.64 (s, 6H), 1.45–1.89 (m, 6H), 0.96 (s, 9H), 0.25 (s, 3H), 0.24 (s, 3H); $^{13}$C NMR (75 MHz, $CDCl_3$) δ156.3 (e), 152.0 (e), 128.9 (c), 125.5 (o), 124.8 (o), 119.5 (o), 119.3 (o), 110.5 (o), 109.9 (o), 103.5 (o), 96.8 (o), 93.1 (e), 92.8 (e), 82.7 (e), 81.6 (e), 80.1 (e), 61.9 (e), 55.3 (o), 54.7 (o), 48.8 (o), 41.5 (e), 36.1 (e), 30.9 (o), 30.2 (e), 25.5 (o), 25.3 (e), 1.9.0 (e), 18.1 (e), −4.3 (o), −4.7 (o); IR ($CHCl_3$) 1687 cm−1; MS (FAB) m/e calculated for $C_{39}H_{51}NO_6Si$: 657.349, found 657.351.

Removal tetrahydropranyl ether to give 20.

Pyridinium p-toluenesulphonate (1.23 g, 4.9 mmol) was added to a solution of the tetrahydropyranyl ether 19 (16.1 g, 24.5 mmol) in ethanol (320 ml) at room temperature and the solution heated at reflux for 18 hours. After cooling the solution to room temperature the solvent was removed under reduced pressure, and water (150 ml) added to the residue. Extraction with diethylether ($1 \times 200$ ml, $2 \times 100$ ml) drying of the combined organic layers over magnesium sulphate and evaporation gave the crude product as a viscous dark brown oil. Flash column chromatography on silica gel eluting with 60% pentane, 40% diethylether (Rf 0.40) yielded 12.58 g (89%) of the desired product 20 as a yellow-green amorphous solid. Alternatively the product was obtained from the crude by crystallization (20% ether-80% pentane, 50 ml, 12.15 g, 86% yield). $^1$H NMR (300 MHz, $CDCl_3$)δ7.44 (s, 1H), 6.63 (dd, J=8.9, 2.7 Hz, 1H), 6.52 (d, J=2.7 Hz, 1H), 5.77 (m, 1H), 5.70–5.80 (m, 1H), 5.68 (m, 1H), 5.64 (s, 1H), 4.27 (s, 2H), 3.77 (s, 3H), 2.15 (s, 9H), 1.64 (s, 6H), 0.96 (s, 3H), 0.26 (s, 3H), 0.25 (s, 3H); $^{13}$C NMR (75 MHz, $CDCl_3$)δ156.3 (e), 152.2 (e), (e), 125.3 (o), 124.8 (e), 119.9 (o), 119.6 (o), 110.5 (o), 109.9 (o), 103.6 (o), 95.3 (e), 93.2 (e), 82.5 (e), 81.9 (e), 80.2 (e), 55.3 (o), 51.3 (e), 48.9 (o), 41.5 (e), 36.1 (e), 30.9 (o), 25.5 (o), 18.1 (e), −4.33 (o), −4.71 (o); IR ($CHCl_3$) 3474, 1685, 1653 cm-1; MS (FAB) m/e calculated for $C_{34}H_{43}NO_5Si$: 579.291, found 573.290.

Cobalt complexation of 20 to give 21.

A solution of dicobalt octacarbonyl (2.67 g, 7.81 mmol) in THF (60 ml) was added rapidly in a single portion to a stirred solution of the propargylic alcohol 20 (4.27 g, 7.44 mmol) in THF (80 ml) at room temperature. After the initial evolution of gas the reaction mixture was stirred at room temperature for 40 minutes then evaporated to give a viscous brown oil. Flash column chromatography on silica gel sequentially eluting with 90% pentane, 10% diethylether gave first a trace of the bis-cobalt complex 23 as a black amorphous solid followed by the desired cobalt regeoisomer 21 3.77 g (59%) as a red-brown amorphous solid. Further elution with 70% pentane, 30% diethyl ether yielded the undesired cobalt regeoisomer 22 2.02 g (33%) as a red brown amorphous solid. Finally elution with 60% pentane, 40% diethylether gave 0.25 g (6%) of the recovered propargylic alcohol 20. For 21 $^1$H NMR (300 MHz, $CDCl_3$) δ7.4 (s, 1H), 6.6–6.72 (m, 2H), 6.54 (d, J=2.8, Hz, 1H), 5.80 (s, 1H), 5.66 (s, 1H), 5.62 (rid, J=10.5, 2.0 Hz, 1H), 4.82 (m, 1H), 4.70 (d, J=14.5 Hz, 1H), 3.77 (s, 3H), 2.16 (s, 9H), 1.65 (s, 6H), 0.95 (s, 9H), 0.25 (s, 3H, 0.24 (s, 3H); $^{13}$C NMR (75 MHz, $CDCl_3$)δ156.5 (e), 152.3 (e), 138.2 (o), 128.9 (e), 125.4 (o), 124.6 (e), 110.7 (o), 110.1 (o), 103.7 (o), 97.7 (e), 96.0 (e), 82.1 (e), 81.8 (e), 81.2 (e), 64.1 (e), 64.0 (e), 55.4 (o), 41.5 (e), 36.1 (e), 30.9 (o), 25.5 (o), 18.1 (e), −4.3 (o), −4.7 (o); IR ($CHCl_3$) 2092, 2056, 2026, 1687, 1655 cm-1; UV-Vis (c=0.0036 mg/ml, $CHCl_3$) λ max$^{243}$ nm (e=$3.3 \times 10^5$).

Recycling incorrect cobalt regioisomer 22.

Ceric ammonium nitrate (5.15 g, 9.40 mmol) was added portionwise over 3 to 4 minutes to a solution of the cobalt complex 22 (2.02 g, 2.35 mmol) and 2,6-ditert-butyl-4-methylpyridine (3.86 g, 18.8 mmol) in acetone (24 ml) at −10° C. After an initial evolution of gas the reaction mixture was stirred for 20 minutes at -10° C. and quenched by the addition of diisopropylethylamine (6.07 g, 47.0 mmol). The resulting dark brown slurry was eluted through a short column of silica gel with 50% diethyl ether, 50% dichloromethane and evaporated to give a viscous brown oil. Flash column chromatography on silica gel eluted with 60% pentane, 40% diethylether (Rf 0.40) yielded 1.03 g (76%) of the propargylic alcohol 20.

Cyclization of 21 to give the [7.3.1]system 24.

Trifluoromethanesulphonic anhydride (1.71 ml, 10.2 mmol) was added rapidly in a single portion to a stirred solution of the cobalt complex 21 (2.18 g, 2.54 mmol) and 2,6-di-tert-butyl-4-methylpyridine (3.13 g, 15.2 mmol) in 2-nitropropane (55 ml) at −10° C. After stirring for 30 minutes at −10° C. the reaction mixture was quenched by the addition of a saturated aqueous solution of sodium bicarbonate solution and the layers separated. Extraction of the aqueous layer with 2-nitropropane (1×15 ml), drying of the combined organic layers over magnesium sulphate, filtration and dilution with acetone (80 ml) gave an opaque red brown solution. After cooling to −10° C., ceric ammonium nitrate (13.93 g, 25.4 mmol) was added portionwise over 3 to 4 minutes. After the initial gas evolution, the reaction mixture was stirred for 20 minutes at −10° C. and quenched by the addition of diisopropylethylamine (8.85 ml, 50.8 mmol). Elution of the reaction mixture through a short column of silica gel with 50% diethylether, 50% dichloromethane followed by evaporation gave a viscous brown oil. Flash column chromatography on silica gel eluted with dichloromethane (Rf 0.50) yielded 0.59 g (53%) of the cyclized enediyne 24 as a white amorphous solid. Recrystalization from dichloromethane-diethylether produced small white prisms. $^1$H NMR (300 MHz, CDCl$_3$) δ7.44 (d, J=8 Hz, 1H), 6.81 (dd, J=2.4, 8.9 Hz, 1H), 6.76 (s, 1H), 5.77 (s, 1H), 5.75 (d, J=9.5, 2.0 Hz, 1H), 5.62 (d, J=9.5 Hz, 1H), 3.79 (s, 3H), 3.68 (A of ABX, 1H), 3.47 (A of ABX, 1H), 3.19 (B of ABX, 1H), 2.13 (s, 9H), 1.64 (s, 6H), $^{13}$C NMR (75 MHz, CDCl$_3$) δ198.5 (e), 157.1 (e), 151.8 (e), 129.5 (e), 129.3 (e), 126.8 (e), 126.3 (e), 121.1 (o), 112.3 (o), 111.6 (o), 99.1 (e), 91.5 (e), 90.0 (e), 83.3 (e), 55.4 (o), 54.2 (o), 49.2 (o), 41.4 (e), 36.0 (e), 30.9 (o), 21.5 (e); IR (CHCl$_3$) 1733, 1696, cm-1; MS FAB m/e calculated for C$_{28}$H$_{28}$NO$_4$: 442.201, found 442.205; base peak 307, parent peak 442, 289, 154, 135.

Removal of adamantyl carbamate to give 25.

Trifluoroacetic acid (2.1 ml, 27.3 mmol) was added dropwise to a stirred solution of the carbamate 24 (481 mg, 1.09 mmol) in dichloromethane (22 ml) at 0° C. The reaction mixture was allowed to warm to room temperature and quenched by the addition of saturated aqueous sodium bicarbonate solution (20 ml) when adjudged to be complete by TLC (silica gel, eluted with 50% pentane 50% diethylether, Rf$_{carbamate}$ 0.50, Rf$_{aniline}$ 0.40), approximately 90 minutes. Extraction with dichloromethane (3×15 ml), drying of the combined organic extracts over magnesium sulphate and evaporation gave a brown amorphous solid. Flash column chromatography on silica gel eluted with 90% dichloromethane, 10% diethyl ether yielded 224 mg (78%) of the aniline 25 as a white amorphous solid. $^1$I NMR (300 MHz, CDCl$_3$) δ6.6–6.8 (m, 3H), 5.78 (d, J=9.2, Hz, 1H), 5.66 (d, J=9.2 Hz, 1H), 4.58 (s, 1H), 3.76 (s, 3H), 3.59 (A of ABX, 1H), 3.55 (A of ABX, 1H), 3.22 (B of ABX, 1H); $^{13}$C NMR (75 MHz, CDCl$_3$) δ199.6 (e), 153.9 (e), 136.3 (e), 125.6 (o), 123.5 (e), 121.2 (o), 117.0 (o), 112.9 (o), 112.4 (o), 99.9 (e), 93.2 (e), 89.9 (e), 82.9 (e), 55.5 (o), 54.2 (o), 48.6 (o), 21.6 (e); MS (FAB) m/e calculated for C$_{17}$H$_{14}$NO$_2$: 264.102, found 264.102; base peak 263, parent peak 263, 234, 220, 154, 136.

EXAMPLE 2

In vivo testing in mice was performed on two 13-ketobicyclo [7.3.1]tridecaenediyne compounds. Both compounds exhibited activity in the P388 leukemia test while one additionally showed significant activity in a solid tumor assay.

P388 Leukemia Assay

In vivo P388 leukemia assays were performed using CDF1 female mice. In experiments, approximately 1×10$^6$ cells were injected intraperitoneally (IP). On day 1 post implant, dose titrations of the compound were administered intraperitoneally (IP) on day 1 post implant only. Each of six animals received a single injection of 64, 32, 16, 8, 4 and 2 mg/kg/dose. Compounds 5582 and 4229 shown in FIG. 8 were tested and compared with Kedarcidin which was employed as a reference compound.

Activity with both compound 5582 and 4229 was observed at an optimal dose of 2 mg per kg, yielding maximal T/C values of 170% and 175% respectively. This compared with kedarcidin which was included as a reference compound and which produced a maximum T/C of 175% at 2.4 mg per kg. Thus the core enediyne dynemicin and its 13-methoxy derivative were active and showed good potency in the P388 leukemia assay when compared with kedarcidin. Results are shown in Table 1.

TABLE I

| | P388 Leukemia Assay | | |
|---|---|---|---|
| Compound | Dose (mg/kg) | % T/C | Survivors |
| 4229 | 64 | toxic | 0/6 |
| | 32 | toxic | 0/6 |
| | 16 | 60 | 6/6 |
| | 8 | 65 | 6/6 |
| | 4 | 65 | 6/6 |
| | 2 | 170 | 6/6 |
| 5582 | 64 | toxic | 0/6 |
| | 32 | 70 | 5/6 |
| | 16 | 60 | 6/6 |
| | 8 | 65 | 6/6 |
| | 4 | 70 | 6/6 |
| | 2 | 175 | 6/6 |
| kedarcidin | 2.4 | 175 | 6/6 |
| | 1.2 | 165 | 6/6 |

Solid Tumor Assay

This assay involves development of a solid tumor in a mouse by injection of M109 tumor cells under the skin of the animal. Solid tumors, typically elliptical in shape, rapidly develop on the flank of the mouse at the site of injection. Progress of the tumor is determined by its size which is measured across each axis of the elongated mass. Straightforward computations of tumor volume combined with an assumed density of 1 g per cc yields a weight estimate which is accepted as an indication of the progress of tumor growth. Increase in lifespan (T/C values) of the animal and delay in tumor growth (T-C) to reach a predetermined size (typically measured as weight of the tumor) are generally accepted by those of skill in the art as endpoint parameters. The clinically tested compounds neocarzinostatin and esperamicin A1 showed increased lifespan and delay in tumor growth, providing standard compounds against which new derivatives and analogs were compared. In the particular M109 assay described and used to test the novel dynemicin analogs, the median time to establish a baseline tumor burden (arbitrarily set at 1 g tumor) was 4 days. Compounds that delayed tumor growth by less than 3 days were considered to lack significant activity.

A standard M109 solid tumor assay was set up to compare compound 5582 and 4229 with neocarzinostatin and esperamicin A1. Female mice were injected subcutaneously with 0.1 mL of a 0.2% brei of M109 tumor cells, prepared from 2 g tumor per 100 mL PBS (phosphate buffered saline).

Figure 9:
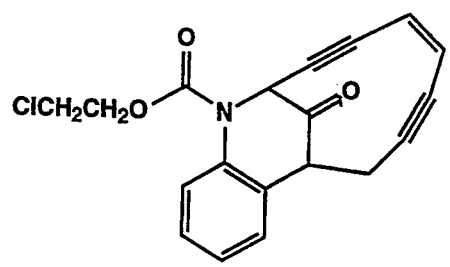
FIG. 9 shows the structures of compounds 5582 and 4429 which are dynemicin core analogs.
Figure 9:
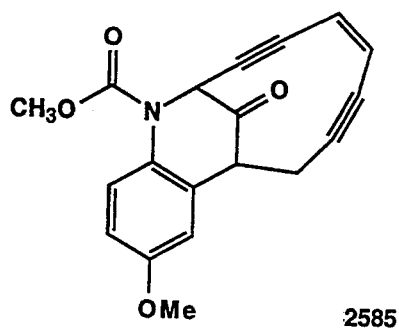
Figure 9:
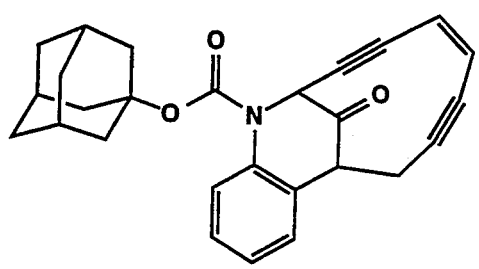
Figure 9:
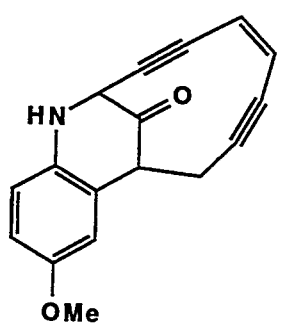
Figure 9:
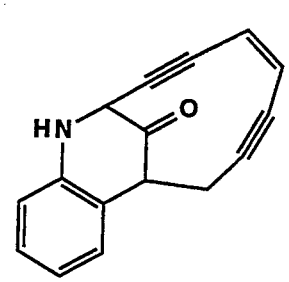

Compound 5582, shown in FIG. 9, was tested in a solid tumor assay compared against kedarcidin as a reference. Results are shown in Table 2.

TABLE 2

| Compound | Solid Tumor M109 Assay | | |
|---|---|---|---|
| | Dose (mg/kg/dose) | %T/C | Survivors |
| 5582 | 0.64 | 106 | 8/8 |
| | 0.32 | 103 | 8/8 |
| | 0.16 | 102 | 8/8 |
| | 0.08 | 97 | 8/8 |
| kedarcidin | 0.04 | 108 | 8/8 |
| | 0.03 | 94 | 8/8 |
| | 0.02 | 106 | 8/8 |
| | 0.01 | 102 | 8/8 |

In another test, compounds 5582 and 4229 were evaluated in mice implanted with M109 on a 5 injection per day every two days schedule beginning on day 1 post implant and compared with SC tumored mice. Neocarzinostatin, which was included as a positive reference compound, produced a T/C value of 19.3 days and esperamicin A1 had a T/C of 11 days. Compound 5582, while not as active as esperamicin A1, nevertheless showed significant activity with a T/C value of 7.5 days, injected at a dose of 1.2 mg/kg/dose five times every two days. Compound 4229, injected at a dose of 0.4 mg/kg/dose five times every two days produced a maximum delay of 3.0 days, indicating only marginal activity.

EXAMPLE 3

The dynemicin core analogs, compounds 4229 and 5582 shown in FIG. 9, were tested for in vitro cytotoxicity.

In Vitro Cytotoxicity

The bicyclo [7.3.1]tridecaenediyne core structure analogs of the antitumor antibiotic dynamicin were tested for in vitro cytotoxicity against. Cytotoxicity was assessed in HCT116 human colon carcinoma cells by XTT (2,3-bis(2-methoxy-4-.nitro-5-sulfophenyl)-5-[(phenylamino)carbonyl]-2H-tetrazolium hydroxide assay (Scudiero, et at., 1988). Cells were plated at 4000 cells/well in 96 well microtiter plates and 24 hrs later drugs were added and serially diluted. The cells were incubated at 37° C. for 72 hrs at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an $IC_{50}$ which is the drug concentration required to inhibit cell proliferation (i.e., absorbance at 450 nm) to 50% of the absorbance of untreated control cells.

Table 3 lists these compounds along with their $IC_{50}$s. Structures are shown in FIG. Compound 4229 had an $IC_{50}$ of 0.21 µM while compound 4230, differing only by an adamantyl carbamyl substituted at the secondary amine group, was less toxic by a factor of over 350, having an $IC_{50}$ of 75 µM.

TABLE 3

| Compound | $IC_{50}$ (µM) |
|---|---|
| 3234 | 4.87 |
| 4230 | 75.0 |
| 2585 | 1.79 |
| 4229 | 0.21 |

EXAMPLE 4

Figure 10:
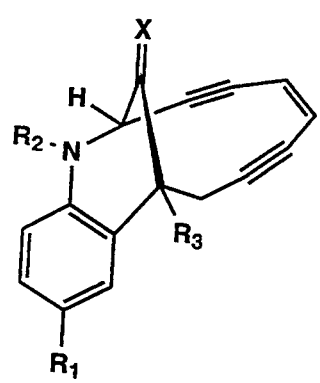
FIG. 10 shows the enediyne dynemicin structure, indicating positions of substitution by reference to the experimental procedure provided in Example 4.

Several derivatives of the core enediyne dynemicin have been synthesized. The structure of the core compound has been substituted at $R_1$, $R_2$, $R_3$ and X at the positions indicated in FIG. 10. For example, $R_1$ may be the usual range of aromatic substitutents such as lower alkyl, halogen, O-alkyls, N-alkyls, S-alkyls. $R_2$ may include carbamates such as alkyl-OCON, Ar—OCON and so forth. $R_3$ is alkyl, including —CH$_2$OMe, SPh, SePh and—CH(OH)Ph. The X group is O, CHCN (both E and Z), —CH$_2$ and —CHCO$_2$Me. Specific synthesis is illustrated.

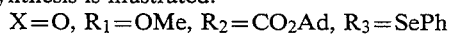

X=O, $R_1$=OMe, $R_2$=CO$_2$Ad, $R_3$=SePh

A solution of lithium hexamethyldisilazane in THF (1.0M, 0.48 mL, 0.48 mmol) was added dropwise to a cold (−78° C.) solution of the carbamate $R_3$=H (192 mg, 0.435 mmol) in THF (3.5 mL). The resulting yellow solution was stirred under argon for 20 min. The lithium enolate was quenched, at −78° C.), by dropwise addition of a solution of phenyl selenide (98%, 140 mg, 0.58 mmol) in THF (0.25 mL). Following 15 min stirring at −78° C., the cooling bath was removed; aq. saturated NH$_4$Cl (2.0 mL) was added to the cold solution. The mixture was diluted with Et$_2$O (8.0 mL), the phases separated and the aqueous phase extracted with Et$_2$O (2×6.0 mL). The combined organic phases were dried (MgSO$_4$) filtered and the solvent removed in vacuo to give the crude product (310 mg). Flash chromatography on silica gel (10.0 g, 20:80 Et$_2$O-pentane) afforded X=O, $R_1$=OMe, $R_2$=CO$_2$Ad, $R_3$=SePh (241 mg, 93% yield) as a pale yellow amorphous solid. R$_f$ 0.36 (2×20:80-ether:pentane); $^1$H NMR (300 MHz, CDCl$_3$) δ7.15-7.50 (m, 6H), 6.74 (dd, J=2.7, 10.0 Hz, 1H), 6.28 (d, J=2.7 Hz, 1H), 5.96 (m, 1H), 5.69 (d, J=9.6 Hz, 1 H), 5.60 (d, J=9.6 Hz, 1H), 3.66 (d, J=17.4 Hz, 1H), 3.59 (s, 3H), 3.31 (d, J=17.4 Hz, 1H), 2.19 (s, 9H), 1.67 (s, 6H); $^{13}$C NMR (75 MHz, CDCl$_3$) δ195.1 (e), 156.9 (e), 156.9 (e), 151.9 (e), 138.4 (o), 130.5 (e), 129.8 (o), 129.1 (o), 128.8 (o), 128.8 (o), 127.9 (o), 127.6 (e), 125.8 (o), 120.8 (o), 113.5 (o), 110.9 (o), 98.5 (e), 92.6 (e), 89.9 (e), 84.3 (e), 82.1 (e), 55.3 (e), 55.2 (o), 41.5 (e), 36.1 (e), 30.9 (e), 27.9 (e); IR (CDCl$_3$) 2913, 1721, 1697, 1496 cm$^{-1}$; mass spec. (FAB) m/z calc'd for C$_{34}$H$_{31}$NO$_4$Se: 597.142, found 597.140; base peak 154, parent peak 597, 554, 440, 396, 368, 307.

X=O, $R_1$=OMe, $R_2$=Co$_2$Ad, $R_3$=CH$_2$COCH$_3$.

A solution of m-chloroperbenzoic acid (80%, 23.2 mg, 0.134 mmol) in CH$_2$Cl2 (0.2 mL) was added dropwise to a stirred solution of the phenyl selenide X=O, $R_1$=OMe, $R_2$=CO$_2$Ad, $R_3$=SePh (59.0 mg, 0.1 mmol), in CH$_2$Cl$_2$ (0.67 mL), under argon at −78 ° C. After the addition the reaction mixture was stirred at −78° C. for 45 min and then treated with 1-(trimethylsilyloxy)-1-methyl ethylene (200 mg, 1.54 mmole) followed by (trimethylsilyl) trifluoromethane sulfonate (33.4 mg, 0.15 mmol). After 10 min at −78 ° C., the temperature was raised to 0 ° C.; aq. saturated NaHCO$_3$ (4.0 mL) was added, the mixture was diluted with CH$_2$Cl$_2$ (4.0 mL) and the phases were separated. The organic phase was washed with aq. saturated NaHCO$_3$ (2.0 mL), dried (MgSO$_4$), filtered and the solvent removed in vacuo, to afford the crude product (79.3 mg). This material was chromatographed on a silica gel plate (1.0 mm thickness, 50:50 Et$_2$O-pentante) to afford the 1,4 diketone X=O, R$_1$=OMe, R$_2$ =Co$_2$Ad, R$_3$=CH$_2$COCH$_3$ (25.0 mg, 51% yield). $^1$H NMR (300 MHz, CDCl$_3$) δ7.22 (m, 1H), 6.82 (dd, J=2.7, 8.9 Hz, 1H), 6.70 (d, J=2.7 Hz, 1H), 6.11 (m, 1H), 5.75 (d, J=9.6 Hz 1H), 5.67 (d, J=9.6 Hz 1H), 3.80 (s, 3H), 3.25 (d, J=24 Hz, 1H), 3.20 (d, J=24 Hz, 1H), 3.0 (m, 2H), 2.18 (s, 9H), 1.86 (s, 3H), 1.65 (s, 6H); $^{13}$C NMR (75 MHz, CDCl$_3$δ202.6 (e), 157.4 (e), 153.4 (e), 133.3 (e), 130.8 (e), 130.8 (e), 128.9 (o), 127.1 (o), 122.1 (o), 118.9 (o), 112.8 (o), 112.0 (o), 99.9 (e), 93.8 (e), 89.9 (e), 84.2 (e), 82.1 (e), 58.2 (e), 56.5 (o), 53.5 (e), 41.8 (e), 36.4 (e), 32.3 (o) 32.2 (e), 30.1 (o); mass spec. (FAB) m/z calc'd for C$_{31}$H$_{31}$NO$_5$: 497.220, found 497.222; base peak 368, parent peak 497, 499, 454, 410, 394, 346.

X=O, R$_1$=OMe, R$_2$=CO$_2$Ad, R$_3$=OH.

The phenyl selenide X=O, R$_1$=OMe, R$_2$=CO$_2$Ad, R$_3$=SePh. (65.5 mg, 0.11 mmol) was dissolved in acetone (3.0 mL) and treated with excess (30–36 equivalents) demethyl dioxirane in acetone. Addition of water (0.2 mL) and warming of the reaction mixture to 40° C. resulted in complete consumption of the intermediate selenoxide within 1 h. The solvent was removed in vacuo, the residue taken up in CH$_2$Cl$_2$ (8.0 mL) and the organic solution was washed with brine (2×4.0 mL). The organic pahse was separated, dried (MgSO$_4$), filtered and the solvent removed in vacuo. The crude product (86 mg) was purified by preparative plate chromatography (silica gel plate, 0.5 mm thickness, 50:50Et$_2$O:pentane) to afford the title compound X=O, R$_1$=OMe, R$_2$=CO$_2$Ad, R$_3$=OH. (34 mg, 68% yield) as an amorphous solid. R$_f$0.33 (50:50-ether:pentane); $^1$H NMR (300 MHz, CDCl$_3$) δ7.45 (d, J=9.0 Hz, 1H), 6.99 (d, J=2.7 Hz, 1H), 6.91 (dd, J=2.7, 9.0 Hz, 1H), 5.98 (d, J=1.8 Hz, 1H), 5.81 (d, J=9.0 Hz, 1H), 5.68 (d, J=1.8, 9.0 Hz, 1H), 3.82 (s, 3H), 3.32 (s, 2H), 308 (m, 1H), 2.17 (s, 3H), 2.13 (s, 6H), (s, 6H); $^{13}$C NMR (75 MHz, CDCl$_3$) δ198.6 (e), 157.5 (e), 151.9 (e), 131.1 (e), 129.7 (e), 127.7 (o), 126.5 (o), 121.3 (o), 115.1 (o), 111.8 (o), 97.1 (e), 91.1 (e), 90.8 (e), 84.9 (e), 82.7 (e), 55.6 (o), 55.3 (o), 41.4 (e), 36.0 (e), 30.9 (o), 30.1 (e); IR (CHCl$_3$) 3750, 1715, 1690 cm$^{-1}$; mass spec. (Cl) m/z calc'd for C$_{28}$H$_{28}$NO$_5$: 458.197, found 458.195; base peak 135, parent peak 458, 460, 442, 398, 326, 285.

X=O, R$_1$=OMe, R$_2$=CO$_2$Ad, R$_3$=OCOPh.

A solution of lithium hexamethyldisilazane in THF (1.0M, 0.3 mL, 0.3 mmol) was added dropwise to a cold (−78° C.) solution of the carbamate R$_3$=H (110 mg, 0.25 mmol) in THF (1.25 mL). The resulting yellow solution was stirred under argon for 35 min, warmed to 0° C. and treated with solid benzoyl peroxide (121 mg, 0.5 mmol). After 18 min at 0° C. aq. saturated NaHCO$_3$ (1.2 mL) was added and the mixture was extracted with Et$_2$O (3×3.0 mL). The combined organic layers were washed with aq. saturated NaHCO$_3$ (3 mL) then with brine (3 mL), dried (MgSO$_4$), and filtered. Filtration and solvent removal in vacuo afforded the crude benzoate (156 mg) as an orange amorphous solid. Flash chromatography on silica gel (7.5 g, 10:90 Et$_2$O-pentane then 30:70-Et$_2$O-pentane) afforded the title compound X=O, R$_1$=OMe, R$_2$=CO$_2$Ad, R$_3$=OCOPh (77.0 mg, 55% yield) as a white amorphous solid. R$_f$ 0.36 (2×20:80-ether:pentane); $^1$H NMR (300 MHz, CDCl$_3$) δ7.92 (d, J=5.7 Hz, 2H), 7.31–7.62 (m, 4H), 6.82–7.22 (m, 2H), 6.25 (m, 1H =9.0 Hz, 1H), 5.75 (dd, J=1.8, 9.0 Hz, 1H), 3.80 (s, 3H), 3.67 (d, J=17.1 Hz, 3.58 (dd, J=17.1, 1.8 Hz, 1H), 2.20 (m, 9H), 1.65 (s, 6H); $^{13}$C NMR (75 MHz, CDCl$_3$) δ195.3 (e), 157.1 (e), 152.4 (e), 133.6 (o), 130.0 (o), 128.3 (o), 125.9 (o), 122.1 (o), 115.0 (o), 112.6 (o), 95.9 (e), 92.9 (e), 89.0 (e), 84.6 (e), 81.9 (e), 78.9 (e), 67.9 (e), 65.8 (e), 55.5 (o), 41.4 (e), 36.2 (e), 30.9 (o), 29.7 (e), 25.7 (e), 16.4 (o), 15.2 (o); mass. spec. (FAB) m/z calc'd for C$_{35}$H$_{31}$NO$_6$: 561.215, found 561.215; base peak 154, parent peak 561, 517, 440, 384.

X=O, R$_1$=OMe, R$_2$=CO$_2$Me, R$_3$=SPh.

To a cooled solution at −78° C. of ene-diyne R$_3$=H (23 mgs, 0.46 mmols) in THF (0.7 mls) was added KHMDS (0.5M in PhMe 0.110 mls 0.055 mmols) and stirred for two minutes. To this solution was added a solution of PhSSO$_2$Ph (13.5 mgs, 0.055 mmols) in THF (mls). The mixture was stirred for a further 10 minutes at −78° C. and quenched with bicarbonate, poured onto ether and washed with bicarb, brine, dried over MgSO$_4$ and evaporated under reduced pressure. Chromatography over silica (Hexane ether 8:2) gave the desired product X=O, R$_1$=OMe, R$_2$=CO$_2$Me, R$_3$=SPh. (22 mgs 78%). $^1$H NMR (300 MHz, CDCl$_3$) δ7.35 (m 2H), 7.24 (s 3H), 7.83 (dd 1H J=2.8, 8.8 Hz), 6.39 (br-s 1H), 5.99 (br-s 1H), 5.71 (d 1H J=10Hz), 5.5.57 (d 1H J=10Hz), 4.77 (td, 1H, J =10.9, 4.4 Hz), 3.65 (s 3H), 3.53 (d 1H J=17.4Hz), 3.23 (dd 1H J=17.4, 1.1Hz), 2.1 (m 2H), 1.8–0.66 (m 16H). $^{13}$C NMR (75 MHz, CDCl$_3$) δ16.19, 21.03, 21.58, 21.99, 23.15, 26.35, 31.43, 34.09, 34.14, 41.13, 41.18, 47.22, 54.78, 55.40, 60.82, 77.18, 84.62, 90.04, 97.89, 101.76, 111.72, 112.14, 113.96, 120.8, 126.02, 126.17, 129.43, 129.56, 130.22, 136.58, 138.04, 157.25. IR (cm-1) (CHCl$_3$) 3027 (w), 3012 (w), 2960 (m), 2930 (m), 2872 (m), 1730 (m), 1705 (s), 1611 (w), 1502 (s). HRMS [Cl+]: 553.227512 (C$_{34}$H$_{35}$NO$_5$S requires 553.228681).

X=O, R$_1$=OMe, R$_2$=H, R$_3$=CH(OH)Ph.

A 1.0M solution of lithium hexamethyldisilazide in tetrahydrofuran (561μ, 55.5 μmol, 1.00 equiv.) was added dropwise to a stirred solution of the bromoaniline X=O, R$_1$=OMe, R$_2$=H, R$_3$=H (19.0 mg, 55.5 μmol, 1.00 equiv.) in anhydrous tetrahydrofuran (2ml) at −78° C. (CO$_{2(S)}$/acetone). Chlorotrimethylsilane (7 μl, 55.5 μmol, 1.00 equiv.) was added after 20 minutes and the clear colourless solution cooled to −95° C. (N$_{2(l)}$/toluene). Distilled benzaldehyde (28 μl, 277 μmol, 5.00 equiv.) followed by a 1.7M solution of t-buytl lithium in pentane (66 μl, 110 μmol, 2.00 equiv.) was added at −95° C. After stirring 15 minutes the cooling bath was removed and the clear brown solution allowed to warm to room temperature and quenched after 30 minutes with saturated aqueous sodium hydrogen carbonate (10 ml). Extraction with dichloromethane (1×10, 2×5 ml), drying of the organic extracts over anhydrous magnesium sulphate and evaporation gave a viscous brown oil ($^1$H NMR indicated a 1:1 mixture of starting material and aldol product, as a single diastereoisomer, with 2,2-dimethyl-1-phenylpropan-1-ol byproduct). The crude reaction mixture was purified by preparative layer chromatography (silica, eluted 2:1 pentane:diethylether, R$_f$; starting material 0.40, aldol product 0.60, 2,2-dimethyl-1-phenylpropan-1 -ol 0.70) to give recovered starting material (5.8 mg, 31%) and aldol product X=O, R$_1$=OMe, R$_2$=H, R$_3$=CH(OB)Ph. (7.0 mg, 34%), as a viscous clear pale yellow oil. IR (C, HCl) 3373 (w), 1732 (s). $^1$H NMR (CDCl$_3$, 300MHz) δ7.25–7.15 (m, 3H), 7.00 (d, J=2.7Hz, 1H), 6.82 (d, J=6.8 Hz, 1H), 5.74 (d, J=2.7 Hz, 1H), 5.70 (dd, J=1.6 and 9.5 Hz, 1H), 5.63 J=9.5 Hz, 1H), 5.04 (s, 1H), 4.65 (d, J=1.8 Hz, 1H), 3.48 (s, 3H), 3.33 (d, J=17.2 Hz, 1H), 2.61 (dd, J=1.6 and 17.2Hz, 1H), −0.16 (s, 9H). $^{13}$C NMR (CDCl$_3$, 75MHz) δ201.98 (e), 152.08 (e), 138.79 (e), 136.27 (e), 128.33 (e), 128.62 (o), 127.25 (o), 125.69 (o), 124.08 (e), 121.49 (o), 117.37 (o), 114.79 (o), 111.14 (e), 99.24 (e), 94.32 (e), 89.06 (e), 82.89 (e), 82.30 (o), 63.51 (e), 55.61 (o), 54.23 (o), 26.26 (e), −0.33 (o). MS (CI) base peak 179, M+H 0.6% base peak. HRMS C$_{27}$H$_{26}$NO$_3$BrSi (M+)calculated 519.086533, found 519.086507 (error 0.1 ppm).

E−X=CHCN, R$_1$=OMe, R$_2$=CO$_2$Ad, R$_3$=H.

A 2.5M solution of n-butyl lithium in hexanes (41 μL, 103 μmol, 1.05 equiv.) was added dropwise to a stirred solution of diethyl cyanomethylphosphonate (17 μL, 108 μmol, 1.10 equiv.) in anhydrous tetrahydrofuran (0.5 ml) at room temperature. After stirring for 40 minutes at room temperature the above clear colourless solution was added dropwise to a stirred solution of the bridgehead ketone X=O, R$_1$=OMe, R$_2$=CO$_2$Ad, R$_3$=H (43.2 mg, 98 μmol, 1.00 equiv.) in tetrahydrofuran (1.5 ml) at 0° C. The resulting clear orange solution was stirred at 0° C. for 20 minutes, eluted through a short column of silica with dichloromethane and evaporated to give a viscous brown oil. Purification of the crude mixture by flash column chromatography (silica, eluted dichloromethane, R$_f$; starting material 0.45, olefinated product 0.55) gave the olefinated product as a white amorphous solid (45.6mg, 85%). IR (CHCl$_3$) 2223 (w), 1694 (s); $^1$H NMR (300MHz, CDCl$_3$) δ7.28–7.42 (m, br, 1H), 6.70–6.80 (m, 2H), 5.91 (s, br, 1H), 5.78 (d, 1H, J=9.4Hz), 5.67 (d 1H, J=9.4Hz), 5.54 (s, 1H), 4.22 (X of ABX, br, 1H), 3.79 (s, 3H), 3.56–3.38 (AB of ABX, 2H), 2.17 (s, 3H), 2.10 (s, 6H) 1.64 (s, 6H); $^{13}$C NMR (75MHz, CDCl$_3$) δ160.49 (e), 156.96 (e), 151.69 (e), 129.45 (e), 129.31 (e), 127.18 (o), 126.54 (o), 121.73 (o), 115.32 (e), 112.43 (o), 111.26 (o), 100.20 (e), 97.26 (o), 94.01 (e), 88.78 (e), 82.33 (e), 83.04 (e), 55.36 (o), 49.40 (o), 41.46 (e), 40.27 (o), 35.98 (e), 30.82 (o), 24.90 (e); MS (CI) base peak m/z 135, (M+H) 3% base peak, HRMS C$_{30}$H$_{28}$N$_2$O$_3$ (M+) calculated 464.209993, found 464.211623 (error 3.5ppm).

X=O, R$_1$=OMe, R$_2$=CO$_2$,Ad, R$_3$=CH,OMe. A 1.0M solution of lithium hexamethyldisilazide in tetrahydrofuran (481 μl, 481 μmol, 1.05 equiv.) was added dropwise to a stirred solution of the bridgehead ketone X=O, R$_1$=OMe, R$_2$=CO$_2$Ad, R$_3$=H (202.2 mg, 458 μmol, 1.00 equiv.) in anhydrous tetrahydrofuran (4 ml) at −78° C. (CO$_{2(S)}$/acetone). The clear pale yellow solution was stirred at −78° C. for 20 minutes and a solution of chloromethyl methylether (104 μl, 1.37mmol, 3.00 equiv.) in tetrahydrofuran (1 ms) was added. After stirring 10 minutes at −78° C. the cooling bath was removed and the clear yellow solution allowed to warm to room temperature. Quenching after 1 hour at room temperature with saturated aqueous sodium hydrogen carbonate (10 ml), extraction with dichloromethane (1×10, 2×5 ml), drying of the organic extracts with anhydrous magnesium sulphate and evaporation gave a viscous orange oil. The crude mixture was purified by flash column chromatography (silica, eluted dichloromethane, R$_f$; starting material 0.45, alkylated product 0.50) to give the alkylated product as a white amorphous solid (180.2 mg, 81%). IR (CHCl$_3$) 1734 (s), 1696 (s); $^1$H (300 MHz, CDCl$_3$) δ7.38 (s, vbr, 1H), 6.82 (dd, br, 1H, J=8.6 and 2.4Hz), 6.73 (d, 1H, J=2.4Hz), 5.75 (s, vbr, 1H), 5.73 (d, 1H, J=9.4Hz), 5.61 (d, 1H, J=9.4Hz), 3.79 (s, 3H), 3.68 (d, 1H, J=7.8Hz), 3.32 (d, br, 1H, J=7.8Hz), 3.16 (d, 1H, J=17.5Hz), 3.05 (s, 3H), 2.91 (dd, 1H, J=17.5 and 1.8Hz), 2.14 (s, 3H), 2.11 (s, 6H), 1.63 (s, 6H); $^{13}$C (75MHz, CDCl$_3$) δ200.27 (e), 157.22 (e), 152.18 (e, br), 132.57 (e, br), 130.64 (e), 127.66 (o), 126.19 (o), 121.23 (o), 112.30 (o), 111.59 (o), 98.26 (e), 91.15 (e, br), 90.82 (e), 83.43 (e), 81.53 (e), 81.22 (e), 59.76 (o), 58.78 (o), 55.42 (o), 41.48 (e), 36.09 (e), 30.87 (o), 25.21 (e), one CH resonance not detected; MS (CI) base peak m/z 135, (M+H) 25% base peak, HRMS (M+) C$_{30}$H$_{31}$NO$_5$ calculated 485.220223, found 485.220290 (error 0.1ppm).

EXAMPLE 5

Figure 1:
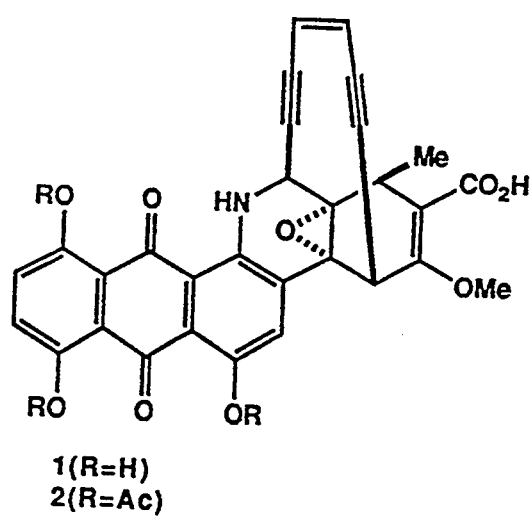
FIG. 1 shows the structure of dynemicin.

An alternative route to the synthesis of compound 6 of FIG. 1 is illustrated below. The advantage of this route is that one need start with 6-methoxyquinoline as a starting material, rather than a 3-hydroxy 6-methoxy quinoline. 6-methoxyquinoline is readily available and is a less expensive starting material.

Preparation of Enol Ether 6

A 1.0M solution of ethylmagnesium bromide in tetrahydrofuran (5 ml, 5 mmol, 1.00 equiv) was added dropwise to a stirred solution of 6-methoxyquinoline (796 mg, 5 mmol, 1 equiv) and enediyne (951 mg, 5 mmol, 1.00 equiv) in anhydrous tetrahydrofuran (40 ml) at 0° C. The clear green solution was stirred for 30 min at 0° C. and a solution of 1-adamantyl chloroformate (1.29 g, 6 mmol, 1.2 equiv) in tetrahydrofuran (10 ml) added dropwise over 2 hrs (syringe pump). On completion of the addition, the cooling bath was removed and the mixture stirred 2 hrs at room temperature, quenched with water (30 ml), filtered, extracted with diethyl ether (1×50, 2×25 ml), the organic extracts dried over anhydrous magnesium sulfate and evaporated to give a viscous brown oil. Purification of the crude mixture by flash column chromatography (silica, eluted 3:1, pentane:diethyl ether, R$_f$; enediyne 0.70, coupled product 0.25, 6-methoxyquinoline 0.20) gave the coupled product as a yellow green foam (1.62 g, 61%).

Meta-chloroperbenzoic acid (153.3 mg, 888 μmol, 3.00 equiv) was added to a rapidly stirred biphasic system of coupled enediyne-quinoline (156.2 mg, 296 μmol, 1.00 equiv), 50% aqueous sodium hydrogen carbonate solution (5 ml) and dichloromethane (5 ml) at room temperature. After stirring for 2 hrs at room temperature, the mixture was extracted with dichloromethane (3×10 ml), the organic extracts dried over anhydrous magnesium sulfate and evaporated to give a viscous yellow oil. Purification of the crude mixture by flash column chromatography (silica eluted 2:1, pentane:diethyl ether, R$_f$; starting material 0.45, epoxide 0.40) yielded the epoxide.

Sodium borohydride (6.6 mg, 174 μmol, 1.25 equiv) was added portionwise over 5 min to a stirred suspension of diphenyl diselenide (65.3 mg, 209 μmol, 1.5 equiv) in absolute ethanol (dried over 4 Å sieves) at room temperature (water bath). After stirring 30 min, the clear yellow solution was added dropwise to a solution of the epoxide (75.8 mg, 139 μmol, 1.00 equiv) in anhydrous tetrahydrofuran (1 ml) at room temperature. The resulting clear orange solution was stirred at room temperature until thin layer chromatography indicated complete consumption of the epoxide (10 hrs). Quenching with water (20 ml), extraction with diethyl ether (1×30, 2×15 ml), drying of the organic extracts over anhydrous magnesium sulfate and evaporation gave a viscous brown oil. Purification of the crude mixture by flash column chromatography (silica, eluted 2:1, pentane:diethyl ether, $R_f$; epoxide 0.40, selenated product 0.30) gave the product as a viscous clear pale yellow oil (63.1 mg, 65%)

A solution of tert-butyldimethylsilyl chloride (17.3 mg, 115 μmol, 1.20 equiv) in anhydrous dimethylformamide (1 ml, dried over 4A sieves) was added dropwise to a solution of the secondary alcohol (67.1 mg, 95.8 μmol, 1.00 equiv), imidazole (13.0 mg, 192 μmol, 2.00 equiv) in dimethylformamide (3 ml) at room temperature. The clear brown solution was stirred 9 hrs at room temperature, drawn-out into water (20 ml), extracted with diethyl ether (1×30, 2×15 ml), the organic extracts dried over anhydrous magnesium sulfate and evaporated to give a yellow semi-solid. Purification of the crude mixture by flash column chromatography (silica, eluted 2:1, pentane:diethyl ether, $R_f$; secondary alcohol 0.40, silyl ether 0.55) gave the silylated product as a viscous clear yellow oil (70.0 mg, 90%).

A solution of meta-perbenzoic acid (11.2 mg, 65.0 μmol, 1.20 equiv) in anhydrous dichloromethane (1 ml) was added dropwise to a stirred solution of the phenyl selenide (45.4 mg, 54.2 μmol, 1.00 equiv) in dichloromethane (1 ml) at 0° C. The mixture was stirred 10 min at 0° C. in pyridine (13 μl, 163 μmol, 3.00 equiv) added and the clear pale yellow solution heated to reflux. After 8 hr at reflux the mixture was cooled to room temperature and evaporated to give a brown oil. Purification of the crude mixture by flash column chromatography (silica, eluted % :1, pentane:diethyl ether, $R_f$; starting material 0.35, product 0.50) gave the silyl enol ether as a yellow foam.

While the compositions and methods of this invention have been described in terms of preferred embodiments, it will be apparent to those of skill in the art that variations may be applied to the composition, methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references, to the extent that they provide exemplary, procedural or other details supplementary to those set forth herein, are specifically incorporated herein by reference.

Green, T., J. Antiobiotics 42, 1449 (1989).
Kamei, H., Nishiyama, Y., Takahashi, A., Obi, Y., Oki, T., J. Antiobiotics 44, 1307 (1991).
Langley, D., Doyle, T., Beveridge, D., J. Am. Chem. Soc. 113, 4395 (1991).
Konishi, M., Ohkuma, H., Matsumoto, K., Saitoh, K., Miyaki, T., Ohi, T. Kawaguchi, H., J. Antiobiotics 44, 1300 (1991).
Konishi, M., Ohkuma, H., Matsumoto, K., Tsuno, T., Kamei, H., Miyaki, T., Oki, T., Kawaguchi, H., Van Duyne, G. D., Clardy, J., J. Antibiotics 42, 1449 (1989).
Konishi, M., Ohkuma, H., Tsuno, T., Oki, T., Van Duyne, G. D., Clardy, J., J. Am. Chem. Soc. 112, 3715 (1990).
Magnus, P., Carter, P., Elliott, J., Lewis, R., Harling, J., Pitterna, T., Bauta, W., Fortt, S., J. Am. Chem. Soc. 114, 2545 (1992).
Magnus, P., Fortt, S., Chem. Commun. 7, 544 (1991).
Magnus, P., Lewis, R., Bennett, F., J. Am. Chem. Soc. 114, 2560 (1992).
Miyashita, N., YHoshikoshi, A., Grieco, P. A., J. Org. Chem. 42, 3772 (1977).
Nicolaou, K., Dai, W., Angew. Chem. Int. Ed. Engl. 30, 1387 (1991).
Nicolaou, K., Dai, W., Tsay, S., Estevez, V., Wrasidlo, W., Science 256, 1171 (1992).
Nicalaou, K., Hong, H., Dai, W., Zeng, Z., Wrasidlo, W., J. Chem. Soc., Chem. Commun. 1542, (1992).
Nicolaou, K., Hwang, C., Smith, A., Wendeborn, S., J. Am. Chem. Soc. 112, 7416 (1990).
Nicolaou, K., Smith, A., Wendeborn, S., Hwang, C., J. Am. Chem. Soc. 113, 3106 (1991).
Porco, J., Schoenen, F., Stout, T., Clardy, J., Schreiber, S., J. Am. Chem. Soc. 112, 7410 (1990).
Scudiero, D. A., Shoemaker, R. H., Paull, K. D., Monks, A., Tierney, S., Nofziger, T. H., Currens, M. J., Seniff, D. and Boyd, M. R., Cancer Res. 48, 4827–4833 (1988).
Semmelhack, M., Gallagher, J. Cohen, D., Tetrahedron Letters 31, No. 11, 1521 (1990).
Smith, A., Hwang, C., Pitsinos, E., Scarlato, G., Nicalaou, K., J. Am. Chem. Soc. 114, 3134 (1992).
Snyder, J., Tipsword, G., J. Am. Chem. Soc. 112, 4040 (1990).
Wood, J., Porco, J., Taunton, J., Lee, A., Clardy, J., Schreiber, S., J. Am. Chem. Soc. 114, 1898 (1992).

What is claimed is:

1. A compound of the formula;

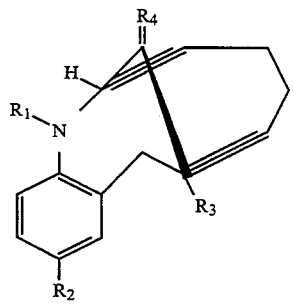

wherein $R_1$ is H, COOAd, COOCH$_2$CH$_2$Cl, COOCH$_3$, CH(CH$_3$)$_2$, cholesterol or menthyl; $R_2$ is H or OCH$_3$; $R_3$ is SePh, CH$_2$COCH$_3$, OH, OCOPh, —SPh, CH(OH) Ph, H or CH$_2$OMe; $R_4$ is CHCH, CH$_2$, O or CHCO$_2$Me except that $R_2$ or $R_3$ is not H when $R_1$ is —COOCH$_3$ and pharmaceutically acceptable salts thereof.

* * * * *

UNITED STATES PATENT AND TRADEMARK OFFICE
CERTIFICATE OF CORRECTION

PATENT NO. : 5,442,065

DATED : August 15, 1995

INVENTOR(S) : Philip D. Magnus, Theodore Iliadis, Shane A. Eisenbeis and Robin A. Fairhurst It is certified that error appears in the above-identified patent and that said Letters Patent is hereby corrected as shown below:

In claim 1, column 26, lines 43-53, delete the figure and replace with

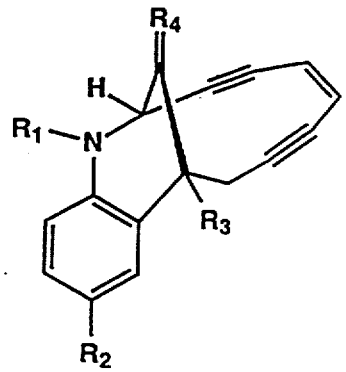

Signed and Sealed this

Twenty-fourth Day of October, 1995

Attest:

BRUCE LEHMAN

Attesting Officer

Commissioner of Patents and Trademarks